(12) United States Patent
Ju

(10) Patent No.: US 7,074,597 B2
(45) Date of Patent: Jul. 11, 2006

(54) MULTIPLEX GENOTYPING USING SOLID PHASE CAPTURABLE DIDEOXYNUCLEOTIDES AND MASS SPECTROMETRY

(75) Inventor: Jingyue Ju, Englewood Cliffs, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 468 days.

(21) Appl. No.: 10/194,882

(22) Filed: Jul. 12, 2002

(65) Prior Publication Data

US 2004/0014042 A1 Jan. 22, 2004

(51) Int. Cl.
*C12P 19/34* (2006.01)
*C12Q 1/68* (2006.01)

(52) U.S. Cl. .................. 435/91.1; 435/6; 435/91.2

(58) Field of Classification Search .............. 435/6, 435/91.1, 91.2
See application file for complete search history.

(56) References Cited

U.S. PATENT DOCUMENTS

| | | |
|---|---|---|
| 4,824,775 A | 4/1989 | Dattagupta |
| 5,118,605 A | 6/1992 | Urdea |
| 5,174,962 A | 12/1992 | Brennan |
| 5,302,509 A | 4/1994 | Cheeseman |
| 5,654,419 A | 8/1997 | Mathies |
| 5,728,528 A | 3/1998 | Mathies |
| 5,770,367 A | 6/1998 | Southern |
| 5,804,386 A | 9/1998 | Ju |
| 5,814,454 A | 9/1998 | Ju |
| 5,834,203 A | 11/1998 | Katzir |
| 5,849,542 A | 12/1998 | Reeve et al. |
| 5,853,992 A | 12/1998 | Glazer |
| 5,869,255 A | 2/1999 | Mathies |
| 5,876,036 A | 3/1999 | Brennan |
| 5,885,775 A | 3/1999 | Haff et al. |
| 5,945,283 A | 8/1999 | Kwok |
| 5,952,180 A | 9/1999 | Ju |
| 6,028,190 A | 2/2000 | Mathies |
| 6,046,005 A | 4/2000 | Ju |
| 6,074,823 A | 6/2000 | Hubert |
| 6,218,118 B1 | 4/2001 | Sampson |
| 6,312,893 B1 | 11/2001 | Van Ness et al. |
| 6,316,230 B1 | 11/2001 | Egholm |
| 6,613,508 B1 | 9/2003 | Ness et al. |
| 2003/0013089 A1* | 1/2003 | Fisher et al. .............. 435/6 |

FOREIGN PATENT DOCUMENTS

| | | |
|---|---|---|
| WO | WO 9106678 | 5/1991 |
| WO | WO 0053805 | 9/2000 |
| WO | WO 0192284 | 12/2001 |
| WO | WO 0222883 | 3/2002 |
| WO | WO 02079519 | 4/2002 |
| WO | WO 0229003 | 10/2002 |

OTHER PUBLICATIONS

Edwards et al. "DNA sequencing using biotinylated dideoxynucleotides and mass spectrometry" Nucleic Acids Research 2001, vol. 29, No. 21 e104.*

(Continued)

*Primary Examiner*—Jezia Riley
(74) *Attorney, Agent, or Firm*—John P. White, Esq.; Cooper & Dunham LLP

(57) ABSTRACT

This invention provides methods for detecting single nucleotide polymorphisms and multiplex genotyping using dideoxynucleotides and mass spectrometry.

18 Claims, 12 Drawing Sheets

OTHER PUBLICATIONS

Hultman et al., Direct Solid Phase Sequencing of Genomic and Plasmid DNA Using Magnetic Beads as Solid Support, *Nucleic Acids Research*, 17(3) :4937-4946.

Axelrod, V. D. et al. (1978) Specific termination of RNA polymerase synthesis as a method of RNA and DNA sequencing. *Nucleic Acids Res*. 5(10) :3549-3563.

Badman, E. R. et al. (2000) A Parallel Miniature Cylindrical Ion Trap Array. *Anal. Chem*. 72:3291-3297.

Badman, E. R. et al. (2000) Cylindrical Ion Trap Array with Mass Selection by Variation in Trap Dimensions. *Anal. Chem*. 72:5079-5086.

Benson, S. C., Mathies, R. A. and Glazer, A. N. (1993) Heterodimeric DNA-binding dyes designed for energy transfer: stability and applications of the DNA complexes. *Nucleic Acids Res*. 21:5720-5726.

Benson, S. C., Singh, P. and Glazer, A. N. (1993) Heterodimeric DNA-binding dyes designed for energy transfer: synthesis and spectroscopic properties. *Nucleic Acids Res*. 21:5727-5735.

Burgess, K. et al. (1997) Photolytic Mass Laddering for Fast Characterization of Oligomers on Single Resin Beads. *J. Org. Chem*. 62:5662-5663.

Canard, B. et al. (1995) Catalytic editing properties of DNA polymerases. *Proc. Natl. Acad. Sci. USA* 92:10859-10863.

Caruthers, M.H. (1985) Gene synthesis machines: DNA chemistry and its uses. *Science* 230:281-285.

Chee, M. et al. (1996) Accessing genetic information with high-density DNA arrays. *Science* 274:610-614.

Chen, X. and Kwok, P.-Y. (1997) Template-directed dye-terminator incorporation (TDI) assay: a homogeneous DNA diagnostic method based on fluorescence resonance energy transfer. *Nucleic Acids Res*. 25:347-353.

Edwards, J. et al. (2001) DNA sequencing using biotinylated dideoxy nucleotides and mass spectrometry. *Nucleic Acids Res*. 29(21):e104.

Griffin, T. J. et al. (1999) Direct Genetic Analysis by Matrix-Assisted Laser Desorption/Ionization Mass Spectrometry. *Proc. Nat. Acad. Sci. USA* 96:6301-6306.

Hacia, J. G., Edgemon, K., Sun, B., Stern, D., Fodor, S. A., and Collins, F.S. (1998) Two Color Hybridization Analysis Using High Density Oligonucleotide Arrays and Energy Transfer Dyes. *Nucleic Acids Res*. 26:3865-6.

Haff, L. A. et al. (1997) Multiplex Genotyping of PCR Products with Mass Tag-Labeled Primers. *Nucleic Acids Res*. 25(18):3749-3750.

Hyman, E. D. (1988), A new method of sequencing DNA. *Analytical Biochemistry* 174:423-436.

Ireland, R. E. and Varney M. D. (1986) Approach to the total synthesis of chlorothricolide—synthesis of (+/−)-19.20-dihydro-24-O-methylchlorothricolide, methyl-ester, ethyl carbonate. *J. Org. Chem*. 51:635-648.

Jiang-Baucom, P. et al. (1997) DNA Typing of Human Leukocyte Antigen Sequence Polymorphisms by Peptide Nucleic Acid Probes and MALDI-TOF Mass Spectrometry. *Anal. Chem*. 69:4894-4896.

Ju, J., Glazer, A. N. and Mathies, R. A. (1996) Energy transfer primers: A new fluorescence labeling paradigm for DNA sequencing and analysis. *Nature Medicine* 2:246-249.

Ju, J., Ruan, C., Fuller, C. W., Glazer, A. N. and Mathies, R. A. (1995) Fluorescence energy transfer dye-labeled primers for DNA sequencing and analysis. *Proc. Natl. Acad. Sci. USA* 92: 4347-4351.

Kamal, A., Laxman, and E., Rao, N. V. (1999) A mild and rapid regeneration of alcohols from their allylic ethers by chlorotrimethylsilane/sodium iodide. *Tetrahedron Lett*. 40: 371-372.

Lee, L. G., et al. (1992) DNA sequencing with dye-labeled terminators and T7 DNA polymerase: effect of dyes and dNTPs on incorporation of dye terminators and probability analysis of termination fragments. *Nucleic Acids Res*. 20:2471-2483.

Lee, L. G. et al. (1997) New energy transfer dyes for DNA sequencing. *Nucleic Acids Res*. 25:2816-2822.

Li, J., (1999) Single Oligonucleotide Polymorphism Determination Using Primer Extension and Time-of-Flight Mass Spectrometry. *Electrophoresis*, 20:1258-1265.

Liu, H. et al., (2000) Development of Multichannel Devices with an Array of Electrospray Tips for High-Throughput Mass Spectrometry. *Anal. Chem*. 72:3303-3310.

Lyamichev, A. et al. (1999) Polymorphism Identification and Quantitative Detection of Genomic DNA by Invasive Cleavage of Oligonucleotide Probes. *Nat. Biotech*. 17:292-296.

Metzker, M. L., et al. (1994) Termination of DNA synthesis by novel 3'-modified deoxyribonucleoside 5'-triphosphates. *Nucleic Acids Res*. 22:4259-4267.

Olejnik, J., et al. (1995) Photocleavable biotin derivatives: a versatile approach for the isolation of biomolecules. *Proc. Natl. Acad. Sci. USA*. 92:7590-7594.

Pelletier, H., Sawaya, M. R., Kumar, A., Wilson, S. H., and Kraut J. (1994) Structures of ternary complexes of rat DNA polymerase β, a DNA template-primer, and ddCTP. *Science* 264:1891-1903.

Prober, J. M., Trainor, G. L., Dam, R. J., Hobbs, F. W., Robertson, C. W., Zagursky, R. J., Cocuzza, A. J., Jensen, M. A., Baumeister K. (1987) A system for rapid DNA sequencing with fluorescent chain-terminating dideoxynucleotides. *Science* 238:336-341.

Ronaghi, M., Uhlen, M., and Nyren, P. (1998) A sequencing Method based on real-time pyrophosphate. *Science* 281:364-365.

Rosenblum, B.B. et al. (1997) New dye-labeled terminators for improved DNA sequencing patterns. *Nucleic Acids Res*. 25:4500-4504.

Ross, P. et al. (1998) High Level Multiplex Genotyping by MALDI-TOF Mass Spectrometry. *Nat. Biotech*. 16:1347-1351.

Ross, P. L. et al. (1997) Discrimination of Single-Nucleotide Polymorphisms in Human DNA Using Peptide Nucleic Acid Probes Detected by MALDI-TOF Mass Spectrometry. *Anal. Chem*. 69:4197-4202.

Saxon, E. and Bertozzi, C. R. (2000) Cell surface engineering by a modified Staudinger reaction. *Science* 287:2007-2010.

Schena, M., Shalon, D., Davis, R., and Brown, P. O. (1995) Quantitative monitoring of gene expression patterns with a complementary DNA microarray. *Science* 270:467-470.

Speicher, M. R., Ballard, S. G. and Ward, D.C. (1986) Karyotyping human chromosomes by combinatorial multi-fluor FISH. *Nature Genetics* 12:368-375.

Stoerker, J. et al. (2000) Rapid Genotyping by MALDI-monitored nuclease selection from probe libraries. *Nat. Biotech*. 18:1213-1216.

Welch, M. B., and Burgess, K. (1999) Synthesis of fluorescent, photolabile 3'-O-protected nucleoside triphosphates for the base addition sequencing scheme. *Nucleosides and Nucleotides* 18:197-201.

Woolley, A. T. et al. (1997) High-Speed DNA Genotyping Using Microfabricated Capillary Array Electrophoresis Chips. *Anal. Chem*. 69:2181-2186.

Fei, Z. et al. (1998) MALDI-TOF mass spectrometric typing of single nucleotide polymorphisms with mass-tagged ddNTPs. Nucleic Acids Research 26(11):2827-2828.

Olejnik, J. et al. (1999) Photocleavable peptide-DNA conjugates: synthesis and applications to DNA analysis using MALDI-MS. *Nucleic Acids Res.* 27(23):4626-4631.

Arbo, et al., (1993) Solid Phase Synthesis of Protected Peptides Using New Cobalt (III) Amine Linkers, *Int. J. Peptide Protein Res.* (1993) 42:138-154.

Bergseid M., Baytan A. R., Wiley J. P., Ankener W. M., Stolowitz, Hughs K. A., Chestnut J. D., (2000) Small-molecule base chemical affinity system for the purification of proteins. *BioTechniques* 29:1126-1133.

Chiu, N. H., Tang, K., Yip, P., Braun, A., Koster, H., and Cantor, C. R., (2000) Mass spectrometry of single-stranded restriction fragments captured by an undigested complementary sequence. *Nucleic Acids Res.* 28:E31.

Fu, D. J., Tang, K., Braun, A., Reuter, D., Darnhofer-Demar, B., Little, D. P., O'Donnell, M. J., Cantor, C.R., and Koster, H., (1998) Sequencing exons 5 to 8 of the p53 gene by MALDI-TOF mass spectrometry. *Nat. Biotechnol.* 16:381-384.

Monforte, J. A., and Becker, C. H., (1997) High-throughput DNA analysis by time-of-flight mass spectrometry. *Nat. Med.* 3(3):360-362.

Roskey, M. T, Juhasz, P., Smirnov, I. P., Takach, E.J., and Martin, S.A., (1996) Haff L.A., DNA sequencing by delayed extraction-matrix-assisted laser desorption/ionization time of flight mass spectrometry. *Proc. Natl. Acad. Sci. USA.* 93:4724-4729.

Tang, K., Fu, D. J., Julien, D., Braun, A., Cantor, C. R., and Koster H., (1999) Chip-based genotyping by mass spectrometry. *Proc. Natl. Acad. Sci. USA.* 96:10016-10020.

Tong, X. and Smith L. M., (1992) Solid-Phase Method for the Purification of DNA Sequencing Reactions. *Anal. Chem.* 64:2672-2677.

U.S. Appl. No. 09/823,181, filed Mar. 30, 2001, Ju et al.

Jingyue Ju, et al. (1996) Cassette labeling for facile construction of energy transfer fluorescent primers. *Nuc. Acids Res.* 24(6):1144-1148.

Jurinke, C., van de Boom, D., Collazo, V., Luchow, A., Jacob, A, Koster, H., (1997) Recovery of nucleic acids from immobilized biotin-streptavidin complexes using ammonium hydroxide and application in MALDI-TOF mass spectrometry. *Anal. Chem.* 69:904-910.

Lee, L. G., Spurgeon, S. L., Heiner, C. R., Benson, S. C., Rosenblum, B. B., Menchen, S. M., Graham, R. J., Constantinescu, A., Upadhya, K. G. and Cassel, J.M. (1997) New energy transfer dyes for DNA sequencing. *Nucleic Acids Res.* 25:2816-2822.

Speicher, M. R., Ballard, S. G. and Ward, D. C. (1996) karyotyping human chromosomes by combinatorial multi-fluor FISH. *Nature Genetics* 12:368-375.

U.S. Appl. No. 09/972,364, filed Oct. 5, 2001.

U.S. Appl. No. 09/684,670, filed Oct. 6, 2000 and.

U.S. Appl. No. 10/194,882, filed Mar. 30, 2001.

\* cited by examiner

MULTIPLEX GENOTYPING USING SOLID PHASE CAPTURABLE DIDEOXYNUCLEOTIDES AND MASS SPECTROMETRY

BACKGROUND OF THE INVENTION

Throughout this application, various publications are referenced in parentheses. Citations for these references may be found at the end of the specification immediately preceding the claims. The disclosures of these publications in their entireties are hereby incorporated by reference into this application to more fully describe the state of the art to which this invention pertains.

Single nucleotide polymorphisms (SNPs), the most common genetic variations in the human genome, are important markers for identifying disease genes and for pharmacogenetic studies (1, 2). SNPs appear in the human genome with an average density of once every 1000-base pairs (3). To perform large-scale SNP genotyping, a rapid, precise and cost-effective method is required. Matrix-assisted laser desorption/ionization time-of-flight mass spectrometry (MALDI-TOF MS) (4) allows rapid and accurate sample measurements (5–7) and has been used in a variety of SNP detection methods including hybridization (8–10), invasive cleavage (11, 12) and single base extension (SBE) (5, 13–17). SBE is widely used for multiplex SNP analysis. In this method, primers designed to anneal immediately adjacent to a polymorphic site are extended by a single dideoxynucleotide that is complementary to the nucleotide at the variable site. By measuring the mass of the resulting extension product, a particular SNP can be identified. Current SBE methods to perform multiplex SNP analysis using MS require unambiguous simultaneous detection of a library of primers and their extension products. However, limitations in resolution and sensitivity of MALDI-TOF MS for longer DNA molecules make it difficult to simultaneously measure DNA fragments over a large mass range (6). The requirement to measure both primers and their extension products in this range limits the scope of multiplexing.

A high fidelity DNA sequencing method has been developed which uses solid phase capturable biotinylated dideoxynucleotides (biotin-ddNTPs) by detection with fluorescence (18) or mass spectrometry (19), eliminating false terminations and excess primers. Combinatorial fluorescence energy transfer tags and biotin-ddNTPs have also been used to detect SNPs (20).

False stops or terminations occur when a deoxynucleotide rather than a dideoxynucleotide terminates a sequencing fragment. It has been shown that false stops and primers which have dimerized can produce peaks in the mass spectra that can mask the actual results preventing accurate base identification (21).

The present application discloses an approach using solid phase capturable biotin-ddNTPs in SBE for multiplex genotyping by MALDI-TOF MS. In this method primers that have different molecular weights and that are specific to the polymorphic sites in the DNA template are extended with biotin-ddNTPs by DNA polymerase to generate 3'-biotinylated DNA extension products. The 3'-biotinylated DNAs are then captured by streptavidin-coated magnetic beads, while the unextended primers and other components in the reaction are washed away. The pure DNA extension products are subsequently released from the magnetic beads, for example by denaturing the biotin-streptavidin interaction with formamide, and analyzed with MALDI-TOF MS. The nucleotide at the polymorphic site is identified by analyzing the mass difference between the primer extension product and an internal mass standard added to the purified DNA products. Since the primer extension products are isolated prior to MS analysis, the resulting mass spectrum is free of non-extended primer peaks and their associated dimers, which increases the accuracy and scope of multiplexing in SNP analysis. The solid phase purification system also facilitates desalting of the captured oligonucleotides. Desalting is critical in sample preparation for MALDI-TOF MS measurement since alkaline and alkaline earth salts can form adducts with DNA fragments that interfere with accurate peak detection (21).

SUMMARY OF THE INVENTION

This invention is directed to a method for determining the identity of a nucleotide present at a predetermined site in a DNA whose sequence immediately 3' of such predetermined site is known which comprises:

(a) treating the DNA with an oligonucleotide primer whose sequence is complementary to such known sequence so that the oligonucleotide primer hybridizes to the DNA and forms a complex in which the 3' end of the oligonucleotide primer is located immediately adjacent to the predetermined site in the DNA;

(b) simultaneously contacting the complex from step (a) with four different labeled dideoxynucleotides, in the presence of a polymerase under conditions permitting a labeled dideoxynucleotide to be added to the 3' end of the primer so as to generate a labeled single base extended primer, wherein each of the four different labeled dideoxynucleotides (i) is complementary to one of the four nucleotides present in the DNA and (ii) has a molecular weight which can be distinguished from the molecular weight of the other three labeled dideoxynucleotides using mass spectrometry; and (c) determining the difference in molecular weight between the labeled single base extended primer and the oligonucleotide primer so as to identify the dideoxynucleotide incorporated into the single base extended primer and thereby determine the identity of the nucleotide present at the predetermined site in the DNA.

In one embodiment, the method further comprises after step (b) the steps of:

(i) contacting the labeled single base extended primer with a surface coated with a compound that specifically interacts with a chemical moiety attached to the dideoxynucleotide by a linker so as to thereby capture the extended primer on the surface; and (ii) treating the labeled single base extended primer so as to release it from the surface.

In one embodiment, the method further comprises after step (i) the step of treating the surface to remove primers that have not been extended by a labeled dideoxynucleotide.

DETAILED DESCRIPTION OF THE INVENTION

Figure 1:
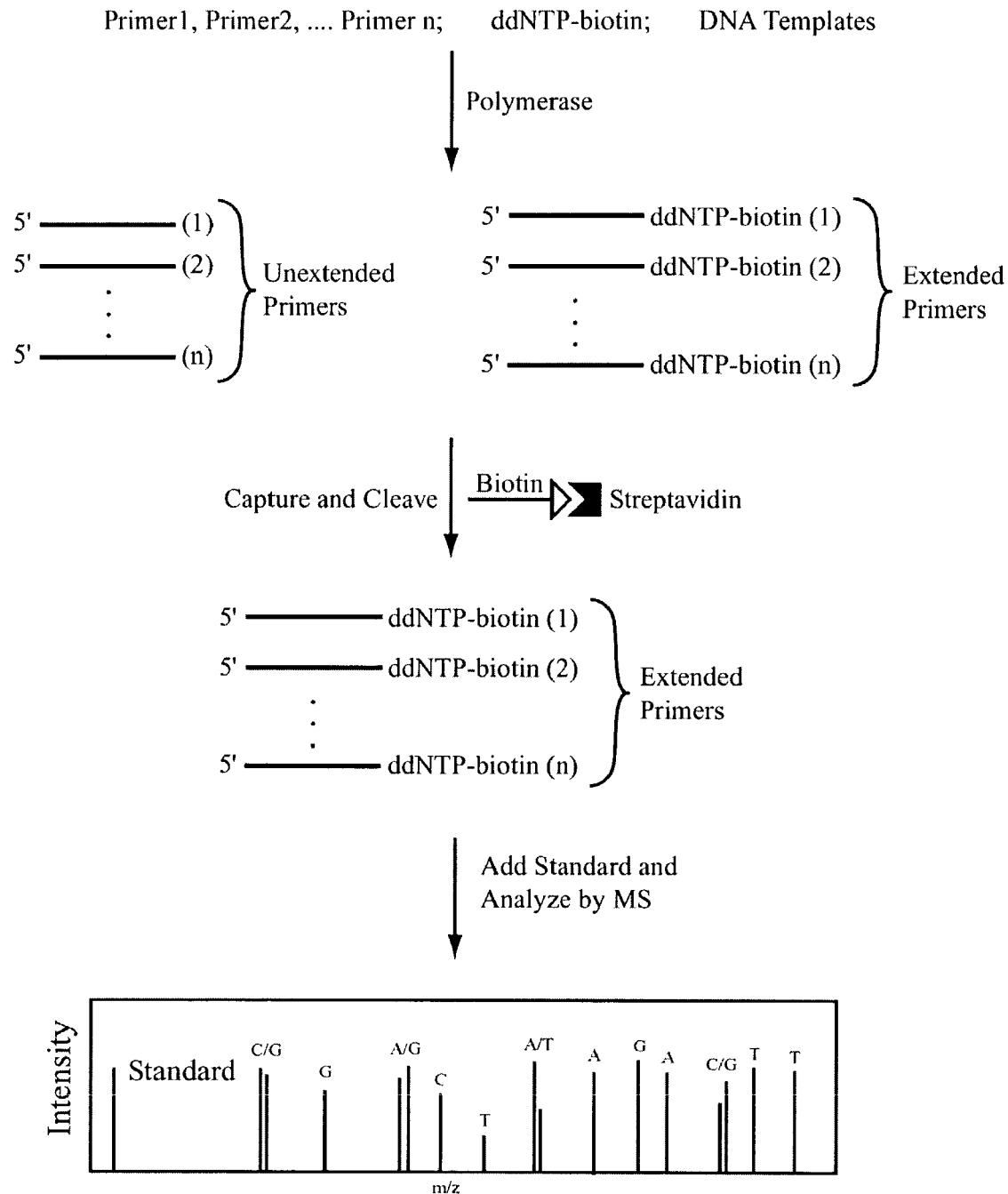
FIG. 1: Scheme of single base extension for multiplex SNP analysis using biotin-ddNTPs and MALDI-TOF MS. Primers that anneal immediately next to the polymorphic sites in the DNA template are extended by DNA polymerase of a biotin-ddNTP in a sequence-specific manner. After solid phase capture and isolation of the 3'-biotinylated DNA extension fragments, MALDI-TOF MS was used to analyze these DNA products to yield a mass spectrum. From the relative mass of each extended primer, compared to the mass of an internal standard, the nucleotide at the polymorphic site is identified.

The following definitions are presented as an aid in understanding this invention.

The standard abbreviations for nucleotide bases are used as follows: adenine (A), cytosine (C), guanine (G), thymine (T), and uracil (U).

A nucleotide analogue refers to a chemical compound that is structurally and functionally similar to the nucleotide, i.e. the nucleotide analogue can be recognized by polymerase as a substrate. That is, for example, a nucleotide analogue comprising adenine or an analogue of adenine should form hydrogen bonds with thymine, a nucleotide analogue comprising C or an analogue of C should form hydrogen bonds with G, a nucleotide analogue comprising G or an analogue of G should form hydrogen bonds with C, and a nucleotide analogue comprising T or an analogue of T should form hydrogen bonds with A, in a double helix format.

This invention is directed to a method for determining the identity of a nucleotide present at a predetermined site in a DNA whose sequence immediately 3' of such predetermined site is known which comprises:

(a) treating the DNA with an oligonucleotide primer whose sequence is complementary to such known sequence so that the oligonucleotide primer hybridizes to the DNA and forms a complex in which the 3' end of the oligonucleotide primer is located immediately adjacent to the predetermined site in the DNA;

(b) simultaneously contacting the complex from step (a) with four different labeled dideoxynucleotides, in the presence of a polymerase under conditions permitting a labeled dideoxynucleotide to be added to the 3' end of the primer so as to generate a labeled single base extended primer, wherein each of the four different labeled dideoxynucleotides (i) is complementary to one of the four nucleotides present in the DNA and (ii) has a molecular weight which can be distinguished from the molecular weight of the other three labeled dideoxynucleotides using mass spectrometry; and (c) determining the difference in molecular weight between the labeled single base extended primer and the oligonucleotide primer so as to identify the dideoxynucleotide incorporated into the single base extended primer and thereby determine the identity of the nucleotide present at the predetermined site in the DNA.

In one embodiment, each of the four labeled dideoxynucleotides comprises a chemical moiety attached to the dideoxynucleotide by a different linker which has a molecular weight different from that of each other linker.

In one embodiment, the method further comprises after step (b) the steps of:

(i) contacting the labeled single base extended primer with a surface coated with a compound that specifically interacts with a chemical moiety attached to the dideoxynucleotide by a linker so as to thereby capture the extended primer on the surface; and (ii) treating the labeled single base extended primer so as to release it from the surface.

In a further embodiment, the method comprises after step (i) the step of treating the surface to remove primers that have not been extended by a labeled dideoxynucleotide and any non-captured component.

In one embodiment of the method step (c) comprises determining the difference in mass between the labeled single base extended primer and an internal mass calibration standard added to the extended primer. In one embodiment, the internal mass standard is 5'-TTTTTCTTTTTCT-3' (SEQ ID NO: 5) (MW=3855 Da).

In one embodiment, the chemical moiety is attached via a different linker to different dideoxynucleotides. In one embodiment, the different linkers increase mass separation between different labeled single base extended primers and thereby increase mass spectrometry resolution.

In one embodiment, the dideoxynucleotide is selected from the group consisting of 2',3'-dideoxyadenosine 5'-triphosphate (ddATP), 2',3'-dideoxyguanosine 5'-triphosphate (ddGTP), 2',3'-dideoxycytidine 5'-triphosphate (ddCTP), and 2',3'-dideoxythymidine 5'-triphosphate (ddTTP).

In different embodiments of the methods described herein, the interaction between the chemical moiety attached to the dideoxynucleotide by the linker and the compound on the surface comprises a biotin-streptavidin interaction, a phenylboronic acid-salicylhydroxamic acid interaction, or an antigen-antibody interaction.

In one embodiment, the step of releasing the labeled single base extended primer from the surface comprises disrupting the interaction between the chemical moiety attached by the linker to the dideoxynucleotide and the compound on the surface. In different embodiments, the interaction is disrupted by a means selected from the group consisting of one or more of a physical means, a chemical means, a physical chemical means, heat, and light. In one embodiment, the interaction is disrupted by light. In one embodiment, the interaction is disrupted by ultraviolet light. In different embodiments, the interaction is disrupted by ammonium hydroxide, formamide, or a change in pH (−log $H^+$ concentration).

In different embodiments, the linker can comprise a chain structure, or a structure comprising one or more rings, or a structure comprising a chain and one or more rings. In different embodiments, the dideoxynucleotide comprises a cytosine or a thymine with a 5-position, or an adenine or a guanine with a 7-position, and the linker is attached to the dideoxynucleotide at the 5-position of cytosine or thymine or at the 7-position of adenine or guanine.

In different embodiments, the step of releasing the labeled single base extended primer from the surface comprises cleaving the linker between the chemical moiety and the dideoxynucleotide. In different embodiments, the linker is cleaved by a means selected from the group consisting of one or more of a physical means, a chemical means, a physical chemical means, heat, and light. In one embodiment, the linker is cleaved by light. In one embodiment, the linker is cleaved by ultraviolet light. In different embodiments, the linker is cleaved by ammonium hydroxide, formamide, or a change in pH (−log $H^+$ concentration).

In one embodiment, the linker comprises a derivative of 4-aminomethyl benzoic acid. In one embodiment, the linker comprises a 2-nitrobenzyl group or a derivative of a 2-nitrobenzyl group. In one embodiment, the linker comprises one or more fluorine atoms.

In one embodiment, the linker is selected from the group consisting of:

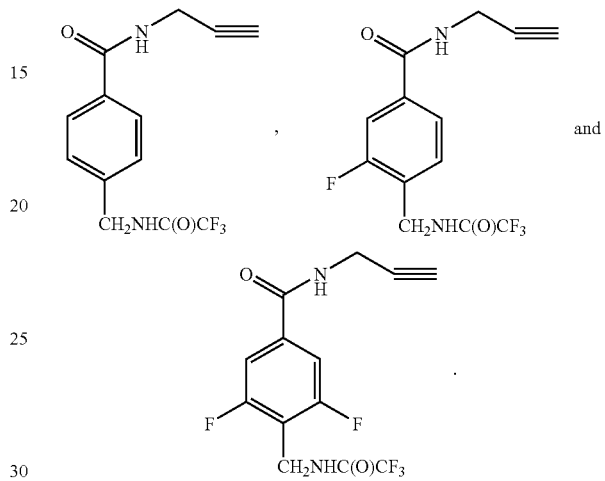

In one embodiment, a plurality of different linkers is used to increase mass separation between different labeled single base extended primers and thereby increase mass spectrometry resolution.

In one embodiment, the chemical moiety comprises biotin, the labeled dideoxynucleotide is a biotinylated dideoxynucleotide, the labeled single base extended primer is a biotinylated single base extended primer, and the surface is a streptavidin-coated solid surface. In one embodiment, the biotinylated dideoxynucleotide is selected from the group consisting of ddATP-11-biotin, ddCTP-11-biotin, ddGTP-11-biotin, and ddTTP-16-biotin.

In one embodiment, the biotinylated dideoxynucleotide is selected from the group consisting of:

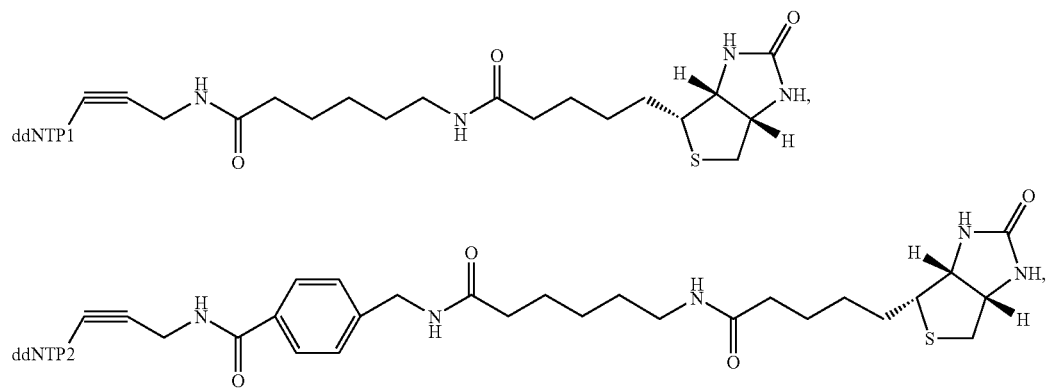

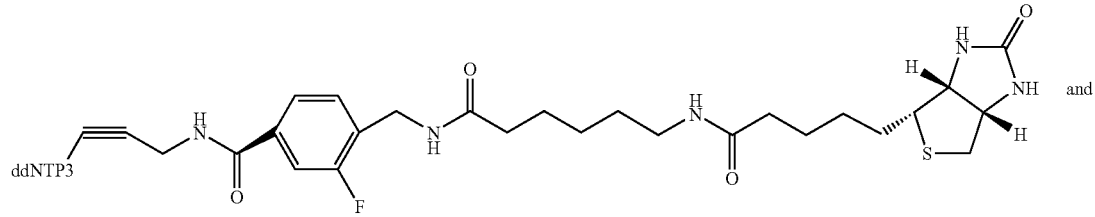
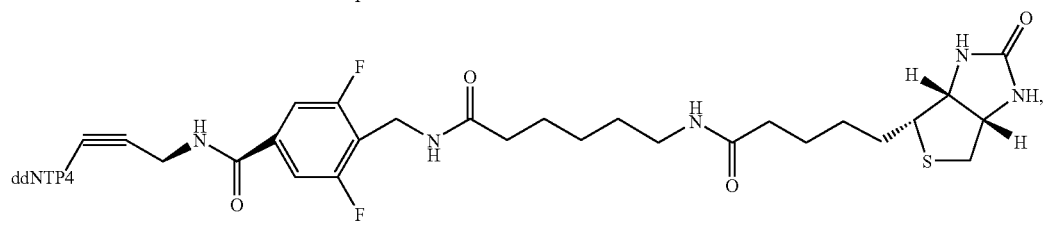
wherein ddNTP1, ddNTP2, ddNTP3, and ddNTP4 represent four different dideoxynucleotides, or their analogues.
In one embodiment, the biotinylated dideoxynucleotide is selected from the group consisting of:
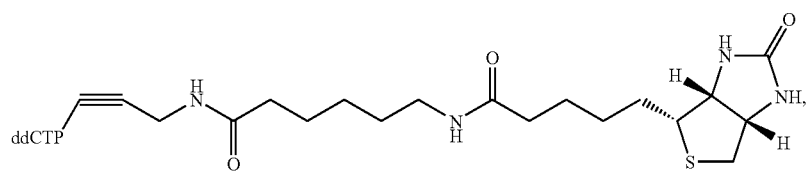
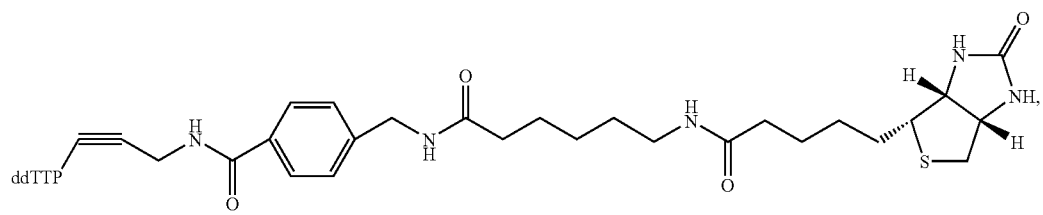
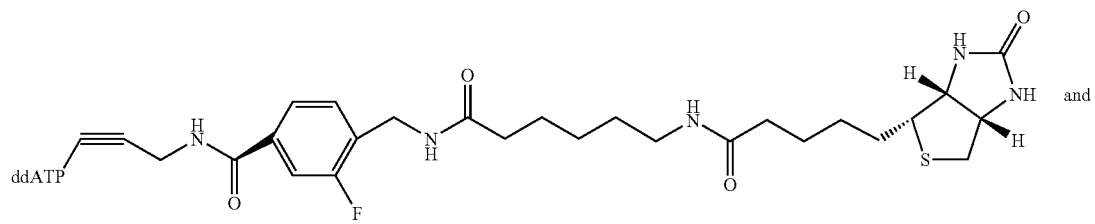
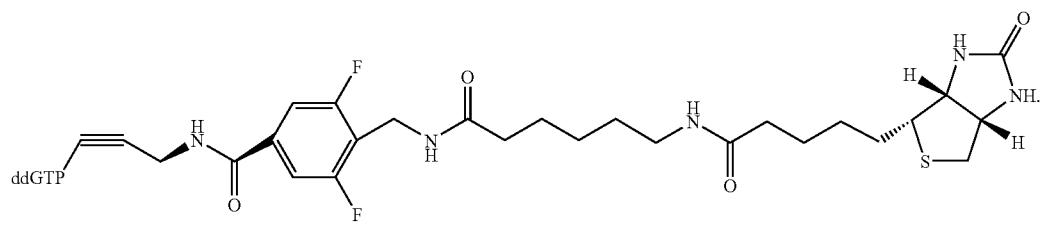

In one embodiment, the biotinylated dideoxynucleotide is selected from the group consisting of:
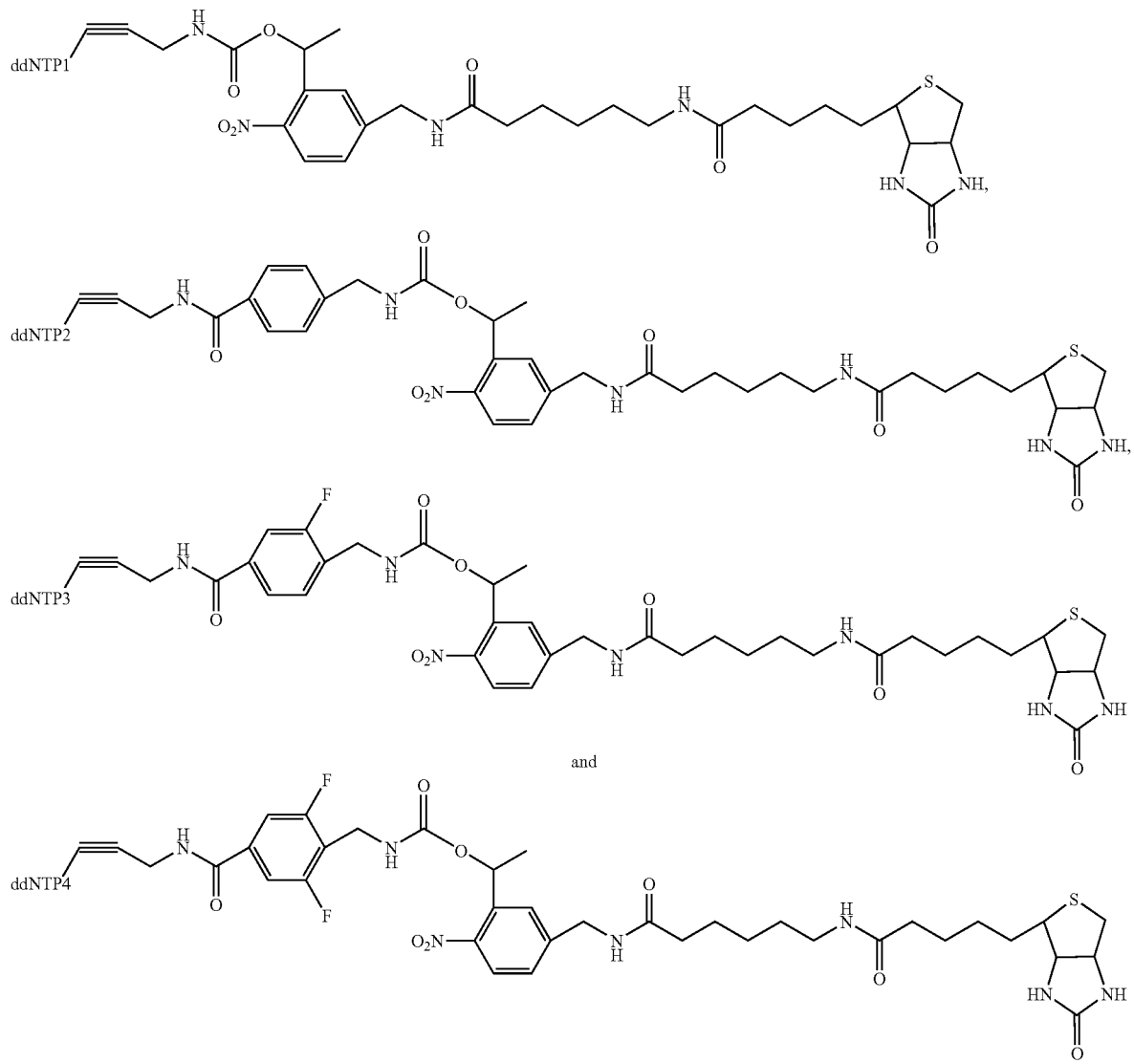
wherein ddNTP1, ddNTP2, ddNTP3, and ddNTP4 represent four different dideoxynucleotides or their analogues.
In one embodiment, the biotinylated dideoxynucleotide is selected from the group consisting of:
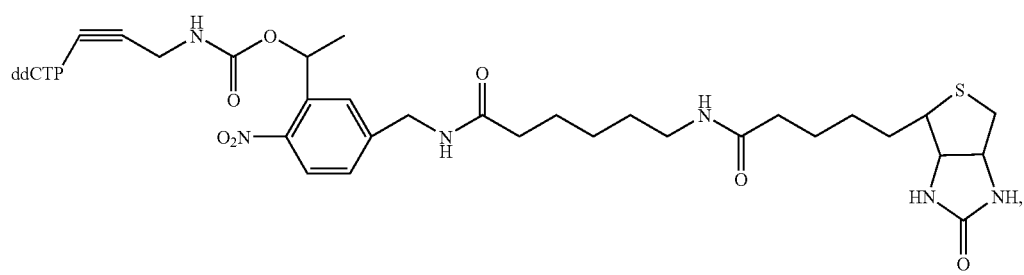

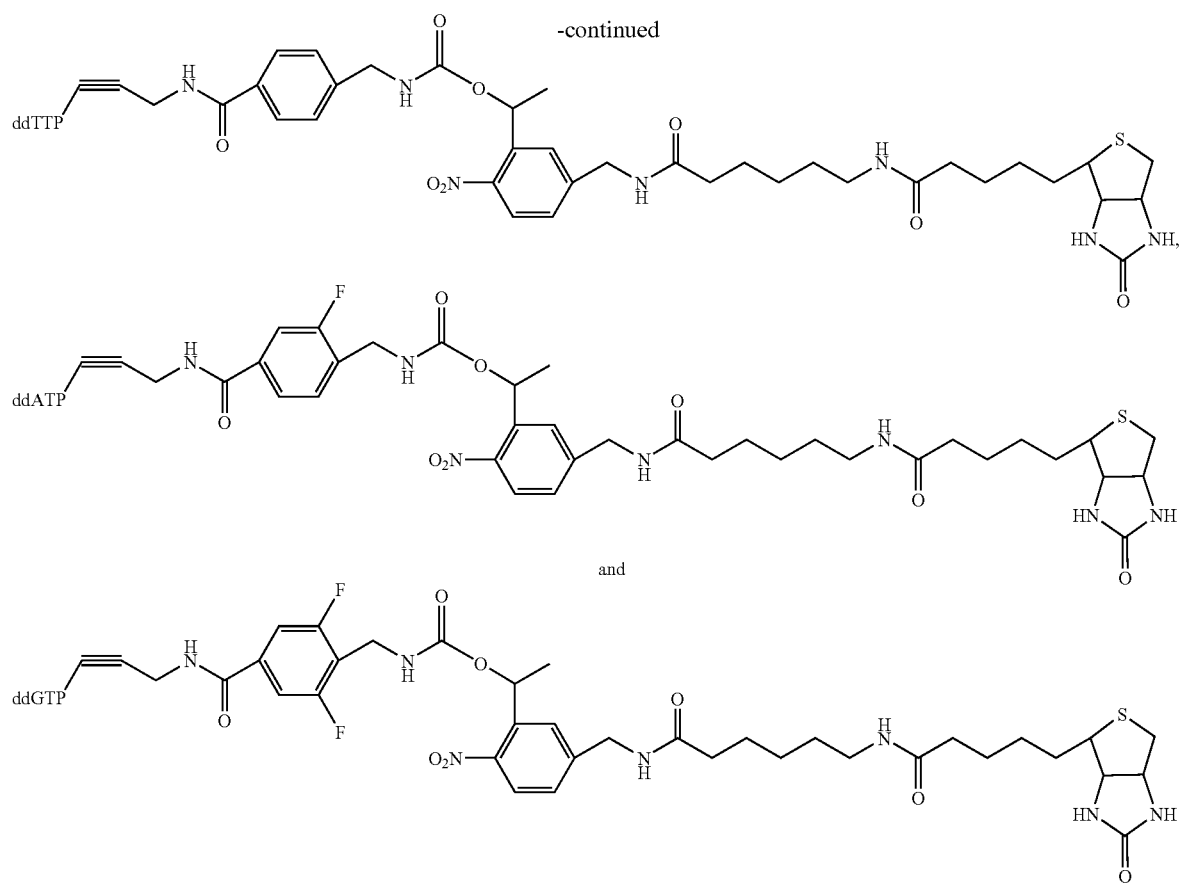

In one embodiment, the streptavidin-coated solid surface is a streptavidin-coated magnetic bead or a streptavidin-coated silica glass.

In one embodiment of the method, steps (a) and (b) are performed in a single container or in a plurality of connected containers.

The invention provides methods for determining the identity of nucleotides present at a plurality of predetermined sites, which comprises carrying out any of the methods disclosed herein using a plurality of different primers each having a molecular weight different from that of each other primer, wherein a different primer hybridizes adjacent to a different predetermined site. In one embodiment, different linkers each having a molecular weight different from that of each other linker are attached to the different dideoxynucleotides to increase mass separation between different labeled single base extended primers and thereby increase mass spectrometry resolution.

In one embodiment, the mass spectrometry is matrix-assisted laser desorption/ionization time-of-flight mass spectrometry.

Linkers are provided for attaching a chemical moiety to a dideoxynucleotide, wherein the linker comprises a derivative of 4-aminomethyl benzoic acid.

In one embodiment, the dideoxynucleotide is selected from the group consisting of 2',3'-dideoxyadenosine 5'-triphosphate (ddATP), 2',3'-dideoxyguanosine 5'-triphosphate (ddGTP), 2',3'-dideoxycytidine 5'-triphosphate (ddCTP), and 2',3'-dideoxythymidine 5'-triphosphate (ddTTP).

In one embodiment, the linker comprises one or more fluorine atoms.

In one embodiment, the linker is selected from the group consisting of:

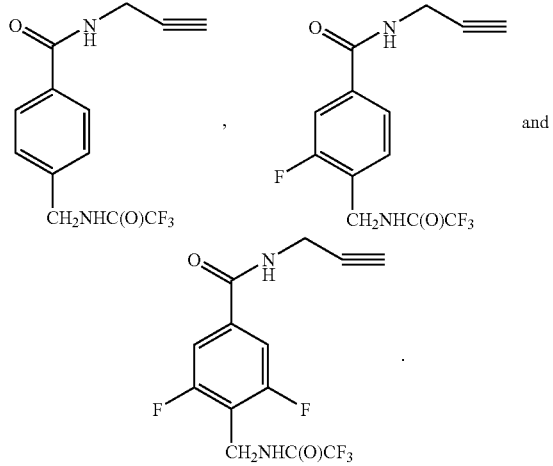

In different embodiments, the linker can comprise a chain structure, or a structure comprising one or more rings, or a structure comprising a chain and one or more rings.

In different embodiments, the linker is cleavable by a means selected from the group consisting of one or more of a physical means, a chemical means, a physical chemical means, heat, and light. In one embodiment, the linker is cleavable by ultraviolet light. In different embodiments, the linker is cleavable by ammonium hydroxide, formamide, or a change in pH (−log H$^+$ concentration)

In different embodiments of the linker, the chemical moiety comprises biotin, streptavidin or related analogues that have affinity with biotin, phenylboronic acid, salicylhydroxamic acid, an antibody, or an antigen.

In different embodiments, the dideoxynucleotide comprises a cytosine or a thymine with a 5-position, or an adenine or a guanine with a 7-position, and the linker is attached to the 5-position of cytosine or thymine or to the 7-position of adenine or guanine.

The invention provides for the use of any of the linkers described herein in single nucleotide polymorphism detection using mass spectrometry, wherein the linker increases mass separation between different dideoxynucleotides and increases mass spectrometry resolution.

Labeled dideoxynucleotides are provided which comprise a chemical moiety attached via a linker to a 5-position of cytosine or thymine or to a 7-position of adenine or guanine.

(ddGTP), 2',3'-dideoxycytidine 5'-triphosphate (ddCTP), and 2',3'-dideoxythymidine 5'-triphosphate (ddTTP).

In different embodiments, the linker can comprise a chain structure, or a structure comprising one or more rings, or a structure comprising a chain and one or more rings. In different embodiments, the linker is cleavable by a means selected from the group consisting of one or more of a physical means, a chemical means, a physical chemical means, heat, and light. In one embodiment, the linker is cleavable by ultraviolet light. In different embodiments, the linker is cleavable by ammonium hydroxide, formamide, or a change in pH −log [H⁺ concentration].

In different embodiments of the labeled dideoxynucleotide, the chemical moiety comprises biotin, streptavidin, phenylboronic acid, salicylhydroxamic acid, an antibody, or an antigen.

In one embodiment, the labeled dideoxynucleotide is selected from the group consisting of:

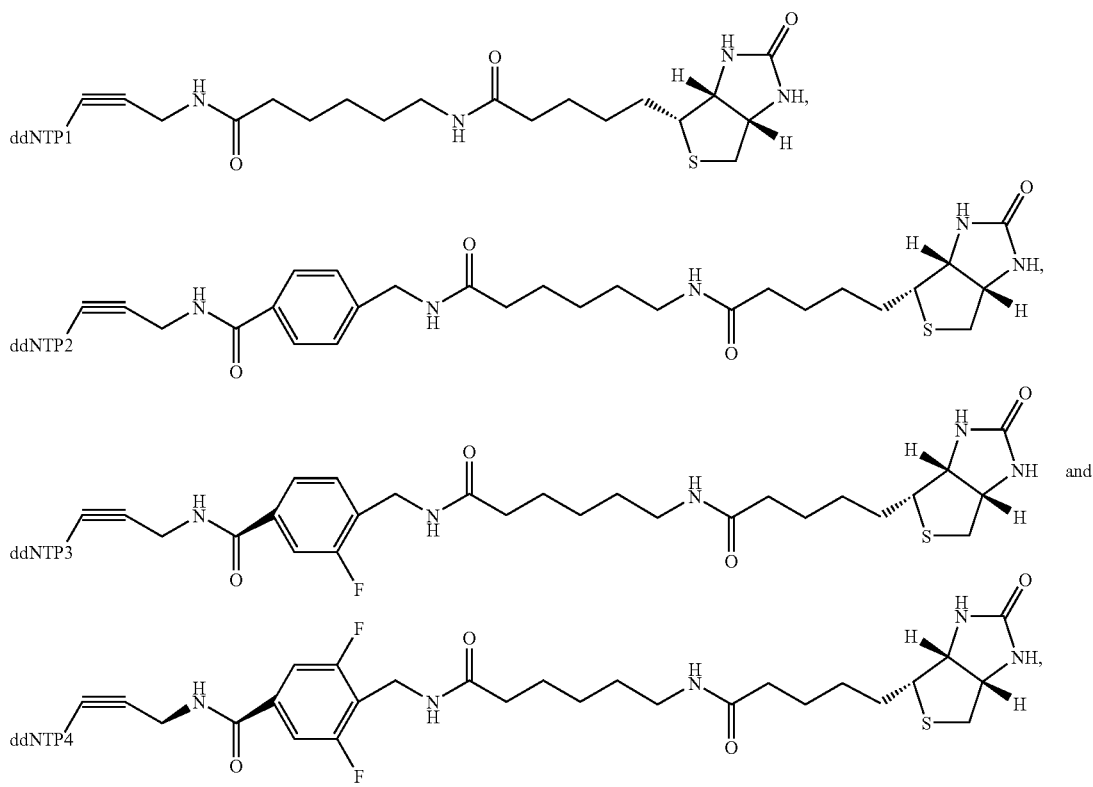

In one embodiment, the dideoxynucleotide is selected from the group consisting of 2',3'-dideoxyadenosine 5'-triphosphate (ddATP), 2',3'-dideoxyguanosine 5'-triphosphate wherein ddNTP1, ddNTP2, ddNTP3, and ddNTP4 represent four different dideoxynucleotides, or their analogues.

In one embodiment, the labeled dideoxynucleotide is selected from the group consisting of:

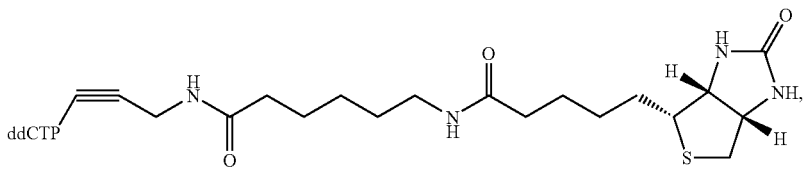

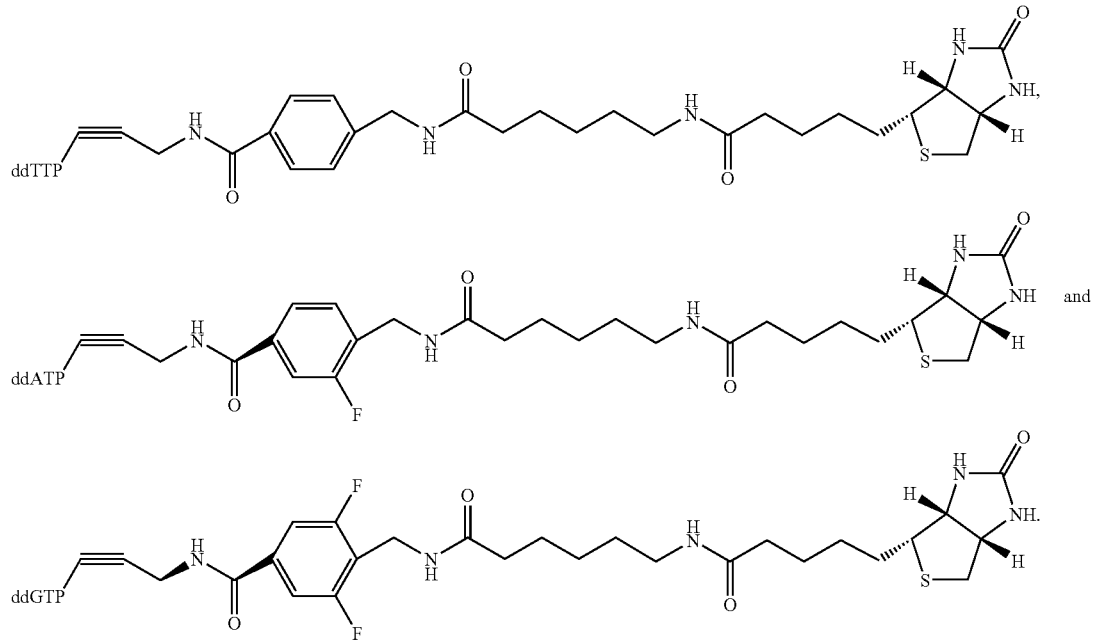
In one embodiment, the labeled dideoxynucleotide is selected from the group consisting of:
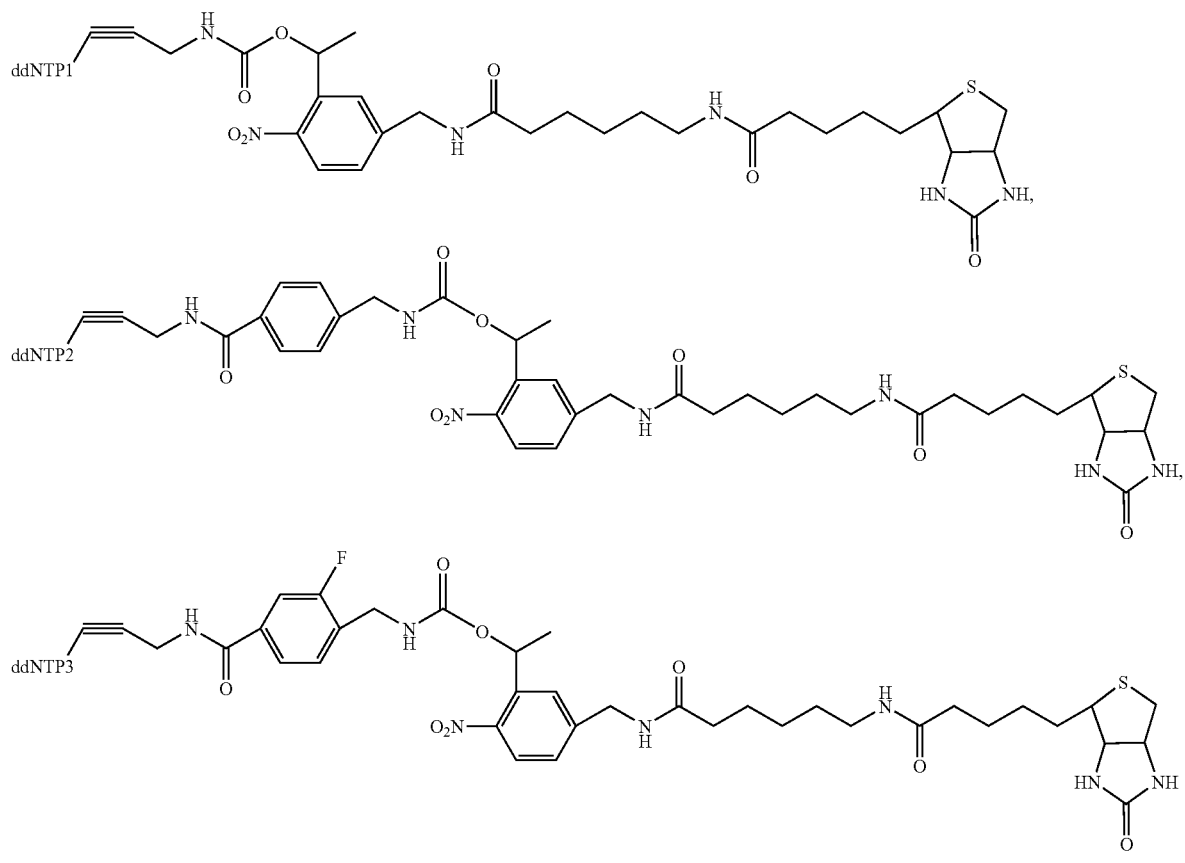
and -continued

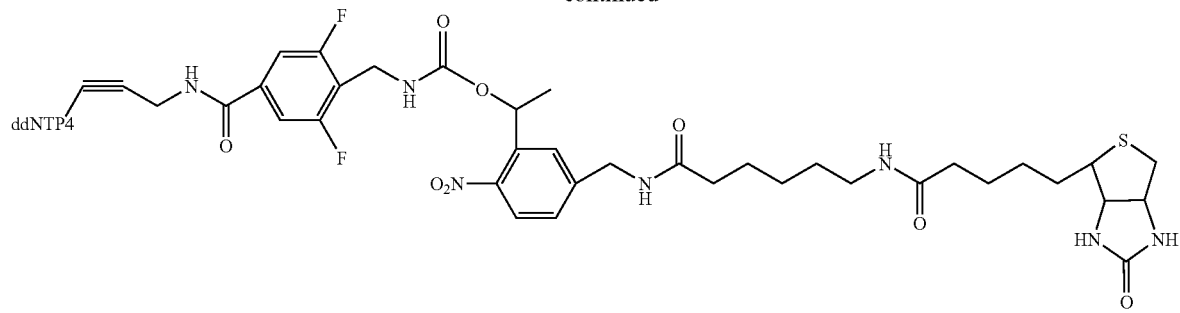

wherein ddNTP1, ddNTP2, ddNTP3, and ddNTP4 represent four different dideoxynucleotides, or their analogues.

In one embodiment, the labeled dideoxynucleotide is selected from the group consisting of:

In one embodiment, the labeled dideoxynucleotide has a molecular weight of 844, 977, 1,017, or 1,051. In one embodiment, the labeled dideoxynucleotide has a molecular weight of 1,049, 1,182, 1,222, or 1,257. Other molecular

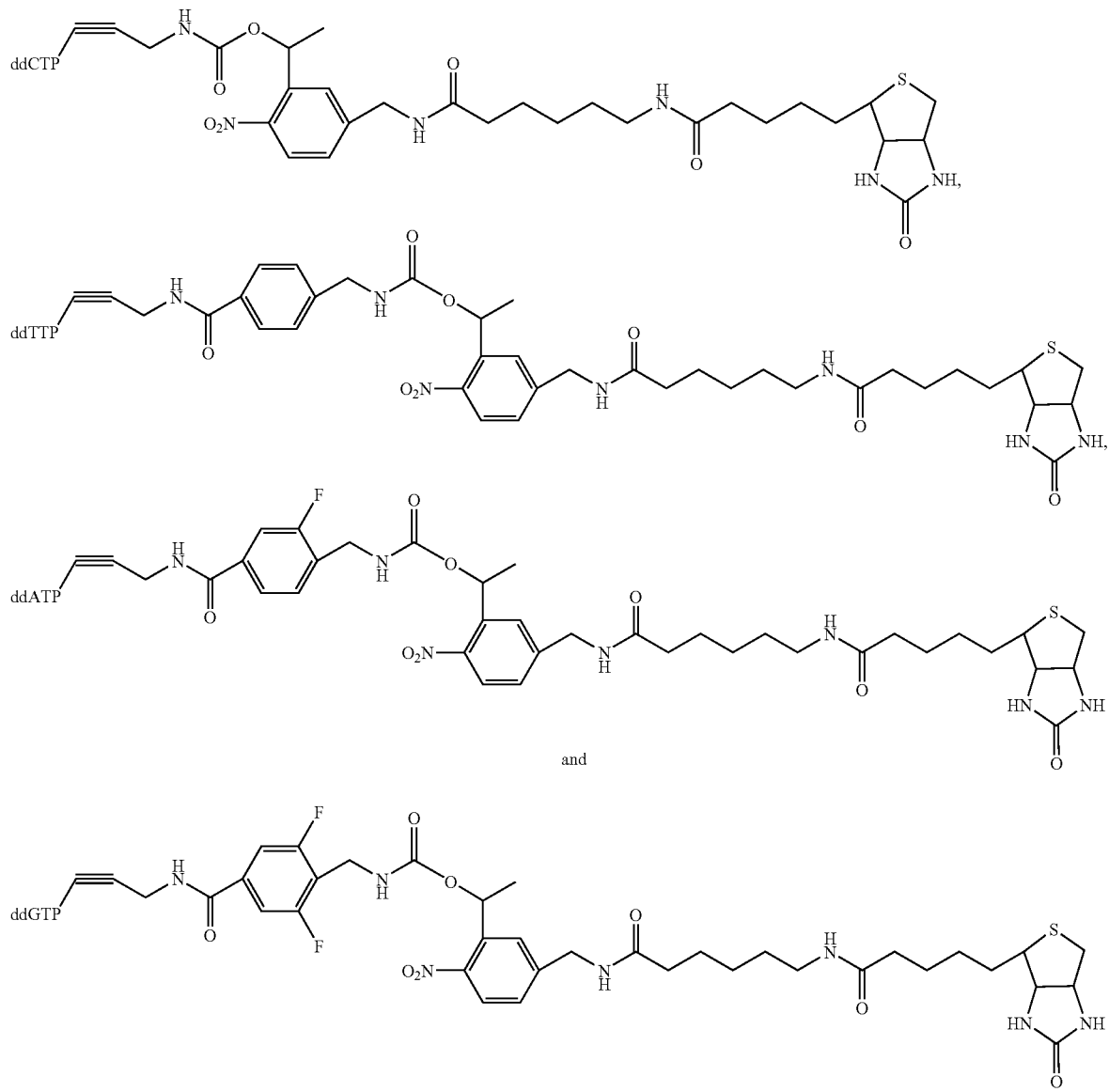

weights with sufficient mass differences to allow resolution in mass spectrometry can also be used.

In one embodiment the mass spectrometry is matrix-assisted laser desorption/ionization time-of-flight mass spectrometry.

A system is provided for separating a chemical moiety from other components in a sample in solution, which comprises:
(a) a channel coated with a compound that specifically interacts with the chemical moiety at the 3' end of the DNA fragment, wherein the channel comprises a plurality of ends;
(b) a plurality of wells each suitable for holding the sample;
(c) a connection between each end of the channel and a well; and
(d) a means for moving the sample through the channel between wells.

In one embodiment of the system, the interaction between the chemical moiety and the compound coating the surface is a biotin-streptavidin interaction, a phenylboronic acid-salicylhydroxamic acid interaction, or an antigen-antibody interaction.

In one embodiment, the chemical moiety is a biotinylated moiety and the channel is a streptavidin-coated silica glass channel. In one embodiment, the biotinylated moiety is a biotinylated DNA fragment.

In one embodiment, the chemical moiety can be freed from the surface by disrupting the interaction between the chemical moiety and the compound coating the surface. In different embodiments, the interaction can be disrupted by a means selected from the group consisting of one or more of a physical means, a chemical means, a physical chemical means, heat, and light. In different embodiments, the interaction can be disrupted by ammonium hydroxide, formamide, or a change in pH −log [$H^+$ concentration].

In one embodiment, the chemical moiety is attached via a linker to another chemical compound. In one embodiment, the other chemical compound is a DNA fragment. In one embodiment, the linker is cleavable by a means selected from the group consisting of one or more of a physical means, a chemical means, a physical chemical means, heat, and light. In one embodiment, the channel is transparent to ultraviolet light and the linker is cleavable by ultraviolet light. Cleaving the linker frees the DNA fragment or other chemical compound from the chemical moiety which remains captured on the surface.

Multi-channel systems are provided which comprise a plurality of any of the single channel systems disclosed herein. In one embodiment, the channels are in a chip. In one embodiment, the multi-channel system comprises 96 channels in a chip. Chips can also be used with fewer or greater than 96 channels.

The invention provides for the use of any of the separation systems described herein for single nucleotide polymorphism detection.

This invention will be better understood from the Experimental Details which follow. However, one skilled in the art will readily appreciate that the specific methods and results discussed are merely illustrative of the invention as described more fully in the claims which follow thereafter.

Experimental Details

I. Materials and Methods

PCR amplification. DNA templates containing the polymorphic sites for the human hereditary hemochromatosis gene HFE were amplified from genomic DNA in a total volume of 10 µl, that contains 20 ng of genomic DNA, 500 pmol each of forward (C282Y; 5'-CTACCCCCAGAACAT-CACC-3' (SEQ ID NO: 1), H63D; 5'-GCACTACCTCT-TCATGGGTGCC-3' (SEQ ID NO: 2)) and reverse (C282Y; 5'-CATCAGTCACATACCCCA-3' (SEQ ID NO: 3), H63D; 5'-CAGTGAACATGTGATCCCACCC-3' (SEQ ID NO: 4)) primers, 25 µM dNTPs (Amersham Biosciences, Piscataway, N.J.), 1 U Taq polymerase (Life Technologies, Rockville, Md.), and 1×PCR buffer (50 mM KCl, 1.5 mM $MgCl_2$, 10 mM Tris-HCl). PCR amplification reactions were started at 94° C. for 4 min, followed by 45 cycles of 94° C. for 30 s, 59° C. for 30 s and 72° C. for 10 s, and finished with an additional extension step of 72° C. for 6 min. Excess primers and dNTPs were degraded by adding 2 U shrimp alkaline phosphatase (Roche Diagnostics, Indianapolis, Ind.) and *E. Coli* exonuclease I (Boehringer Mannheim, Indianapolis, Ind.) in 1× shrimp alkaline phosphatase buffer. The reaction mixture was incubated at 37° C. for 45 min followed by enzyme inactivation at 95° C. for 15 min.

Single base extension using biotin-ddNTPs. The synthetic DNA templates containing six nucleotide variations in p53 gene and the five primers for detecting these variations are shown in Table 1.

These oligonucleotides and an internal mass standard (5'-TTTTTCTTTTTCT-3' (SEQ ID NO: 5), MW=3855 Da) for MALDI-TOF MS measurement were made using an Expedite nucleic acid synthesizer (Applied Biosystems, Foster City, Calif.). SBE reactions contained 20 pmol of primer, 10 pmol of biotin-11-ddATP, 20 pmol of biotin-11-ddGTP, 40 pmol of biotin-11-ddCTP (New England Nuclear Life Science, Boston, Mass.), 80 pmol of biotin-16-ddUTP (Enzo Diagnostics, Inc., Farmingdale, N.Y.), 2 µl Thermo Sequenase reaction buffer, 1 U Thermo Sequenase in its diluted buffer (Amersham Biosciences) and 20 pmol of either synthetic template or 10 µl PCR product in a total reaction volume of 20 µl. For SBE using synthetic template 1, 10 pmol of both wild type and mutated templates were combined with 20 pmol of primers 1 and 3 or 20 pmol of primers 2 and 4. The SBE reaction of primer 5 was performed with template 2 in a separate tube. PCR products from the HFE gene were mixed with 20 pmol of the corresponding primers 5'-GGGGAAGAGCA-GAGATATACGT-3' (SEQ ID NO: 6) (C282Y) and 5'-GGGGCTCCACACGGCGACTCTC-AT-3' (SEQ ID NO: 7) (H63D) in SBE to detect the two heterozygous genotypes. All extension reactions were thermalcycled for 35 cycles at 94° C. for 10 s and 49° C. for 30 s.

Solid phase purification. 20 µl of the streptavidin-coated magnetic beads (Seradyn, Ramsey, Minn.) were washed with modified binding and washing (B/W) buffer (0.5 mM Tris-HCl buffer, 2 M $NH_4Cl$, 1 mM EDTA, pH 7.0) and resuspended in 20 µl modified B/W buffer. Extension reaction mixtures of primers 1–4 with template 1 and primer 5 with template 2 were mixed in a 2:1 ratio, while extension reaction mixtures from the PCR products of HFE gene were mixed in equal amounts. 20 µl of each mixed extension product was added to the suspended beads and incubated for 1 hour. After capture, the beads were washed twice with modified B/W buffer, twice with 0.2 M triethyl ammonium acetate (TEAA) buffer and twice with deionized water. The primer extension products were released from the magnetic beads by treatment with 8 µl 98% formamide solution containing 2% 0.2 M TEAA buffer at 94° C. for 5 min. The released primer extension products were precipitated with 100% ethanol at 4° C. for 30 min, and centrifuged at 4° C. and 14000 RPM for 35 min.

MALDI-TOF MS analysis. The purified primer extension products were dried and re-suspended in 1 µl deionized water and 2 µl matrix solution. The matrix solution was made by dissolving 35 mg of 3-hydroxypicolinic acid (3-HPA; Aldrich, Milwaukee, Wis.) and 6 mg of ammonium citrate (Aldrich) in 0.8 ml of 50% acetonitrile. 10 pmol internal mass standard in 1 µl of 50% acetonitrile was then added to the sample. 0.5 µl of this mixture containing the primer extension products and internal standard was spotted on a stainless steel sample plate, air-dried and analyzed using an Applied Biosystems Voyager DE Pro MALDI-TOF mass spectrometer. All measurements were taken in linear positive ion mode with a 25 kV accelerating voltage, a 94% grid voltage and a 350 ns delay time. The obtained spectra were processed using the Voyager data analysis package.

II. Detection of Single Nucleotide Polymorphism Using Biotinylated Dideoxynucleotides and Mass Spectrometry Solid phase capturable biotinylated dideoxynucleotides (biotin-ddNTPs) were used in single base extension for multiplex genotyping by mass spectrometry (MS). In this method, oligonucleotide primers that have different molecular weights and that are specific to the polymorphic sites in the DNA template are extended with biotin-ddNTPs by DNA polymerase to generate 3'-biotinylated DNA extension products (FIG. 1). These products are then captured by streptavidin-coated solid phase magnetic beads, while the unextended primers and other components in the reaction are washed away. The pure extension DNA products are subsequently released from the solid phase and analyzed with matrix-assisted laser desorption/ionization time-of-flight MS. The mass of the extension DNA products is determined using a stable oligonucleotide as a common internal mass standard. Since only the pure extension DNA products are introduced to MS for analysis, the resulting mass spectrum is free of non-extended primer peaks and their associated dimers, which increases the accuracy and scope of multiplexing in single nucleotide polymorphism (SNP) analysis. The solid phase purification approach also facilitates desalting of the captured oligonucleotides, which is essential for accurate mass measurement by MS.

Four biotin-ddNTPs with distinct molecular weights were selected to generate extension products that have a two-fold increase in mass difference compared to that with conventional ddNTPs. This increase in mass difference provides improved resolution and accuracy in detecting heterozygotes in the mass spectrum.

The "lock and key" functionality of biotin and streptavidin is often utilized in biological sample preparation as a way to remove undesired impurities (23). In different embodiments of the methods described herein, affinity systems other than biotin-streptavidin can be used. Such affinity systems include but are not limited to phenylboronic acid-salicylhydroxamic acid (31) and antigen-antibody systems.

The multiplex genotyping approach was validated by detecting six nucleotide variations from synthetic DNA templates that mimic mutations in exons 7 and 8 of the p53 gene. Sequences of the templates and the corresponding primers are shown in Table 1 along with the masses of the primers and their extension products. The mass increase of the resulting single base extension products in comparison with the primers is 665 Da for addition of biotin-ddCTP, 688 Da for addition of biotin-ddATP, 704 Da for addition of biotin-ddGTP and 754 Da for addition of biotin-ddUTP. The mass data in Table 1 indicate that the smallest mass difference among any possible extensions of a primer is 16 Da (between biotin-ddATP and biotin-ddGTP). This is a substantial increase over the smallest mass difference between extension products using standard ddNTPs (9 Da between ddATP and ddTTP). This mass increase yields improved resolution of the peaks in the mass spectrum. Increased mass difference in ddNTPs fosters accurate detection of heterozygous genotypes (15), since an A/T heterozygote with a mass difference of 9 Da using conventional ddNTPs can not be well resolved in the MALDI-TOF mass spectra. The five primers for each polymorphic site were designed to produce extension products without overlapping masses. Primers extended by biotin-ddNTPs were purified and analyzed by MALDI-TOF MS according to the scheme in FIG. 1. Extension products of all five primers were well-resolved in the mass spectrum free from any unextended primers (FIG. 2A), allowing each nucleotide variation to be unambiguously identified. Unextended primers occupy the mass range in the mass spectrum decreasing the scope of multiplexing, and excess primers can dimerize to form false peaks in the mass spectrum (21). The excess primers and their associated dimers also compete for the ion current, reducing the detection sensitivity of MS for the desired DNA fragments. These complications were completely removed by carrying out SBE using biotin-ddNTPs and solid phase capture. Extension products for all four biotin-ddNTPs were clearly detected with well resolved mass values. The relative masses of the primer extension products in comparison to the internal mass standard revealed the identity of each nucleotide at the polymorphic site. In the case of heterozygous genotypes, two peaks, one corresponding to each allele (C/A), are clearly distinguishable in the mass spectrum shown in FIG. 2A.

TABLE 1

Oligonucleotide primers and synthetic DNA templates for detecting mutations in the p53 gene.
(Top) The sequences and the calculated masses of primers and the four possible single base extension products relative to the internal mass standard are listed.
The bold numbers refer to the nucleotide variations detected in the p53 gene.
(Bottom) The six nucleotide variations in template 1 and 2 are shown in bold letters.
Template 1 contains a heterozygous genotype (G/T).
Primers 1–5 = SEQ ID NOs: 8–12, respectively.

| | | | Masses of single base extension products (Da) | | | |
|---|---|---|---|---|---|---|
| Primers | Primer sequences | Masses (Da) | Biotin-ddCTP Δ665 | Biotin-ddATP Δ688 | Biotin-ddGTP Δ704 | Biotin-ddUTP Δ754 |
| 1 | 5'-AGAGGATCCAACCGAGAC-3' | 1656 | 2321 | 2344 | 2360 | 2410 |
| 2 | 5'-TGGTGGTAGGTGATGTTGATGTA-3' | 3350 | 4015 | 4038 | 4054 | 4103 |

TABLE 1-continued

| 3 | 5'-CACATTGTCAAGGACGTACCCG-3' | 2833 | 3498 | 3521 | 3538 | 3587 |
| 4 | 5'-TACCCGCCGTACTTGGCCTC-3' | 2134 | 2799 | 2822 | 2838 | 2480 |
| 5 | 5'-TCCACGCACAAACACGGACAG-3' | 2507 | 3172 | 3195 | 3211 | 3261 |

Templates Template sequences 1  5'-TACCCG/TGAGGCCAAGTACGGCGGGTACGTCCTTGACAATGTGTACATCAACATCACCTACCACCATGTCAGT (SEQ ID NO: 13)
   CTCGGTTGGATCCTCTATTGTGTCCGGG-3'

2  5'-GAAGGAGACACGCGGCCAGAGAGGGTCCTGTCCGTGTTTGTGCGTGGAGTTTCGACAAGGCAGGGTCATCTAAT (SEQ ID NO: 14)
   GGTGATGAGTCCTATCCTTTTCTCTTCGTTCTCCGT-3'

One advantage of MALDI-TOF MS in comparison to other detection techniques is its ability to simultaneously measure masses of DNA fragments over a certain range.

In order to explore this feature to detect multiple SNPs in a single spectrum, if unextended primers are not removed, masses of all primers and their extension products must have sufficient differences to yield adequately resolved peaks in the mass spectrum. Ross et al. simultaneously detected multiple SNPs by carefully tuning the masses of all primers and extension products so that they would lie in the range of 4.5 kDa and 7.6 kDa without overlapping (14). Since the unextended primers occupy the mass range in the mass spectrum, by eliminating them, the approach disclosed herein will significantly increase the scope of multiplexing in SNP analysis.

Figure 2:
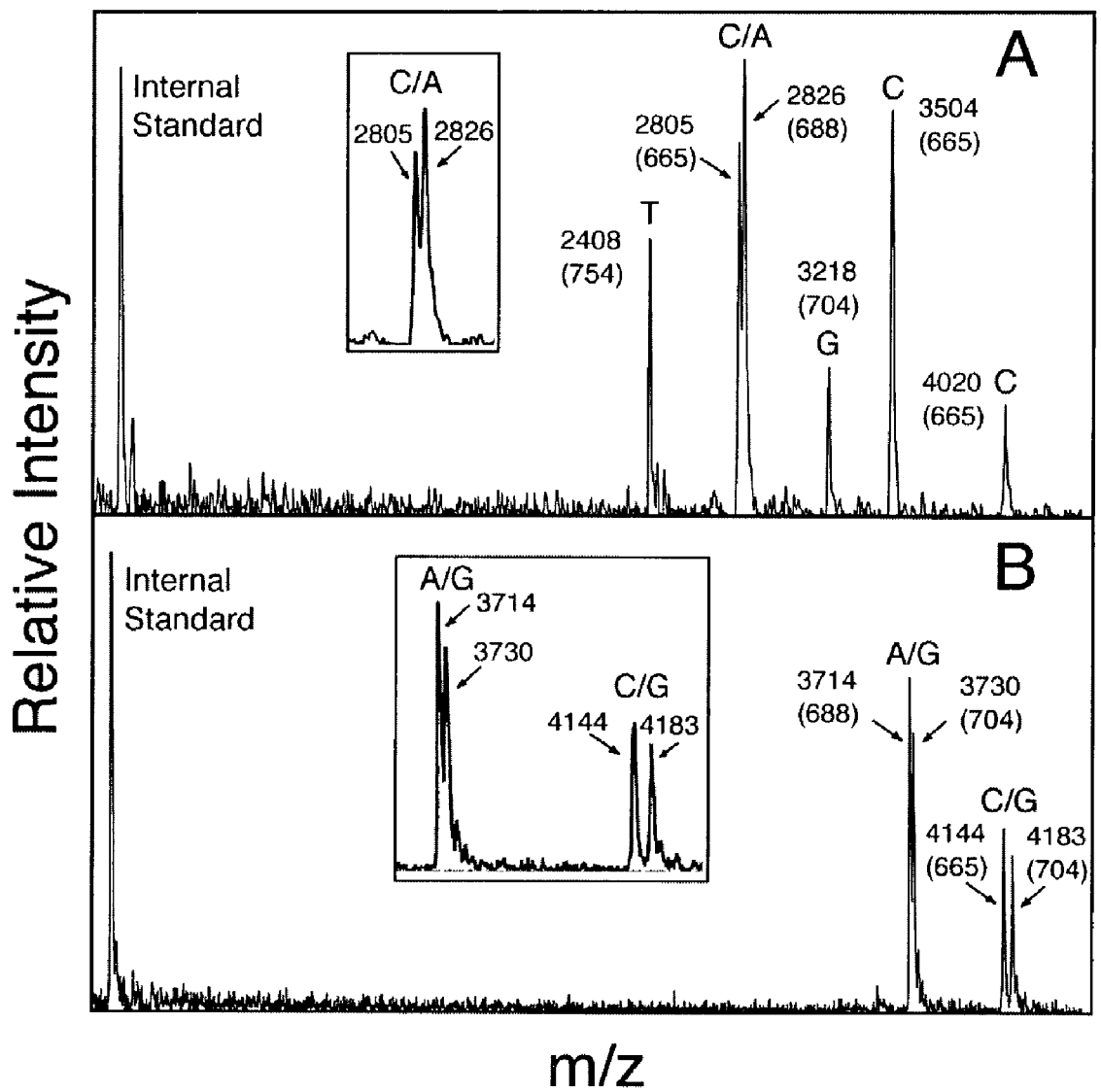
FIG. 2. Multiplex SNP genotyping mass spectra generated using biotin-ddNTPs. Inset is a magnified view of heterozygote peaks. Masses of the extension product in reference to the internal mass standard were listed on each single base extension peak. The mass values in parenthesis indicate the mass difference between the extension products and the corresponding primers. (A) Detection of six nucleotide variations from synthetic DNA templates mimicking mutations in the p53 gene. Four homozygous (T, G, C and C) and one heterozygous (C/A) genotypes were detected. (B) Detection of two heterozygotes (A/G and C/G) in the human HFE gene.

To demonstrate the ability of this method to discriminate SNPs in genomic DNA, two disease associated SNPs were genotyped in the human hereditary hemochromatosis (HHC) gene HFE. HHC is a common genetic condition in Caucasians with approximately 1/400 Caucasians homozygous for the C282Y mutation leading to iron overload and potentially liver failure, diabetes and depression (22). A subset of individuals who are compound heterozygotes for the C282Y and H63D mutations also manifest iron overload. Because of the high prevalence of these mutations and the ability to prevent disease manifestations by phlebotomy, accurate methods for genotyping these two SNPs will foster genetic screening for this condition. Two PCR products were generated from human genomic DNA for the C282Y and H63D polymorphic sites of the HFE gene and then used these products for SBE with biotin-ddNTPs. After the extension reaction, products were purified using solid phase capture according to the scheme in FIG. 1 and analyzed by MALDI-TOF MS. The mass spectrum obtained from this experiment is shown in FIG. 2B. Extension products of each primer were readily identified by their mass relative to the internal mass standard. Heterozygous genotypes of A/G and C/G with a mass difference of 16 Da and 39 Da respectively were accurately detected at the C282Y and H63D polymorphic sites.

These results indicate that the use of solid phase capturable biotin-ddNTPs in SBE, coupled with MALDI-TOF MS detection, provides a rapid and accurate method for multiplex SNP detection over broad mass ranges and should greatly increase the number of SNPs that can be detected simultaneously. In multiplex SBE reactions, the oligonucleotide primers and their dideoxynucleotide extension products differ by only one base pair, which requires analytical techniques with high resolution to resolve. In addition, a primer designed to detect one polymorphism and an extension product from another polymorphic site may have the same size, which can not be separated by electrophoresis and other conventional chromatographic or size exclusion methods. Methods for purifying DNA samples using the strong interaction of biotin and streptavidin are widely used (23–27). By introducing the biotin moiety at the 3' end of DNA, the solid phase based affinity purification approach described here is a unique and effective method to remove the oligonucleotide primers from the dideoxynucleotide extension products.

To increase the stability of DNA fragments for MALDI-TOF MS measurement in multiplex SNP analysis, nucleotide analogues (28) and peptide nucleic acid (9) can be used in the construction of the oligonucleotide primers. It has been shown that MALDI-TOF MS could detect DNA fragments up to 100 bp with sufficient resolution (29). The mass difference between each adjacent DNA fragment is approximately 300 Da. Thus, with a mass difference of 100 Da for each primer in designing a multiplex SNP analysis project, at least 300 SNPs can be analyzed in a single spot of the sample plate by MS. It is a routine method now to place 384 spots in each sample plate in MS analysis. Thus, each plate can produce over 100,000 SNPs, which is roughly the entire SNPs in all the coding regions of the human genome. This level of multiplexing should be achievable by mass tagging the primers with stable chemical groups in SBE using biotin-ddNTPs. For SNP sites of interest, a master database of primers and the resulting masses of all four possible extension products can be constructed. The experimental data from MALDI-TOF MS can then be compared with this database to precisely identify the library of SNPs automatically. This method coupled with future improvements in mass spectrometer detector sensitivity (30) will provide a platform for high-throughput SNP identification unrivaled in speed and accuracy.

III. Design and Synthesis of Biotinylated Dideoxynucleotides with Mass Tags

Figure 3:
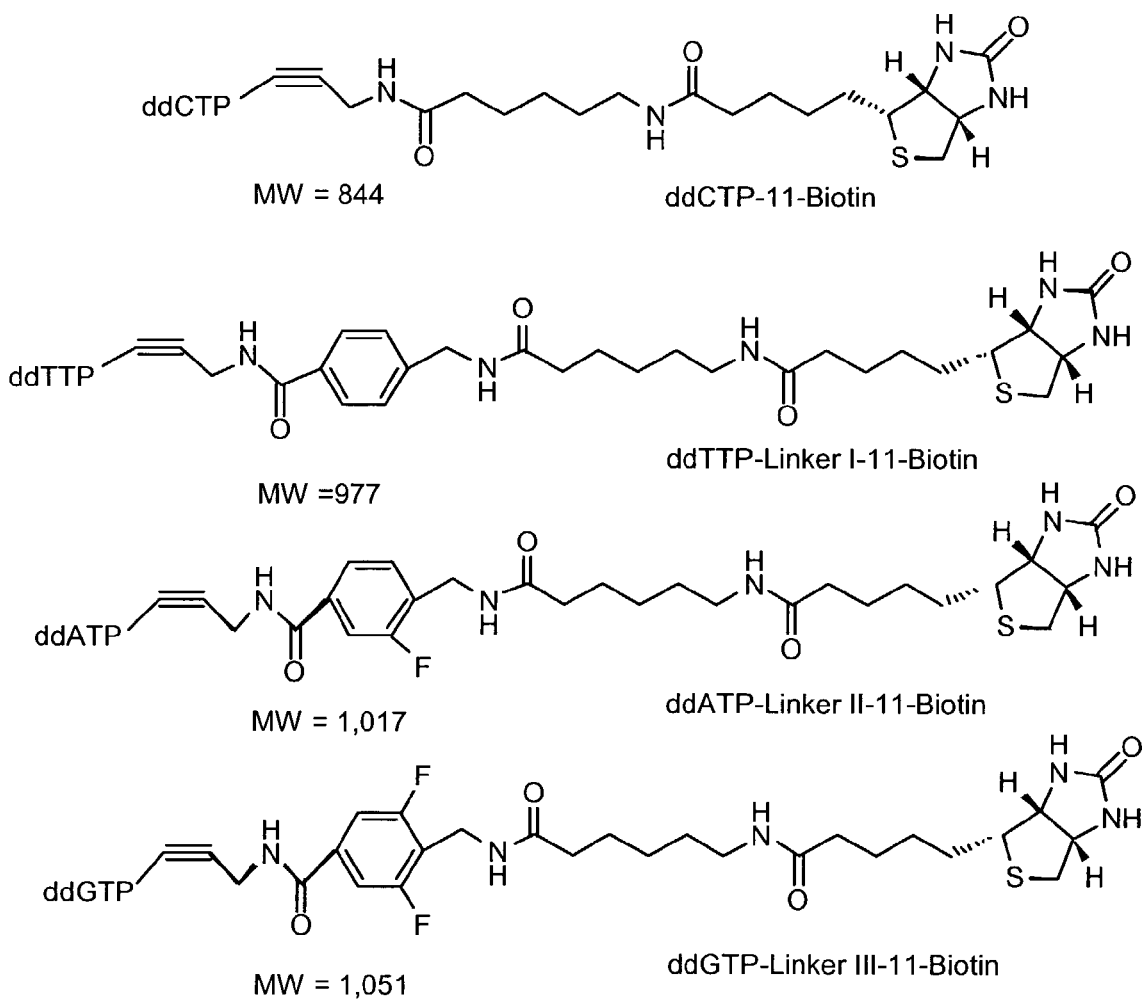
FIG. 3: Structure of four mass tagged biotinylated ddNTPs. Any of the four ddNTPs (ddATP, ddCTP, ddGTP, ddTTP) can be used with any of the illustrated linkers.

The ability to distinguish various bases in DNA using mass spectrometry is dependent on the mass differences of the bases in the spectra. For the above work, the smallest difference in mass between any two nucleotides is 16 daltons (see Table 1). Fei et al. (15) have shown that using dye-labeled ddNTP paired with a regular dNTP to space out the mass difference, an increase in the detection resolution in a single nucleotide extension assay can be achieved. To enhance the ability to distinguish peaks in the spectra, the current application discloses systematic modification of the biotinylated dideoxynucleotides by incorporating mass linkers assembled using 4-aminomethyl benzoic acid derivatives to increase the mass separation of the individual bases. The mass linkers can be modified by incorporating one or two fluorine atoms to further space out the mass differences between the nucleotides. The structures of four biotinylated ddNTPs are shown in FIG. 3. ddCTP-11-biotin is commercially available (New England Nuclear, Boston). ddTTP-Linker I-11-Biotin, ddATP-Linker II-11-Biotin and ddGTP-Linker III-11-Biotin are synthesized as shown, for example, for ddATP-Linker II-11-Biotin in FIG. 5. In designing these mass tag linker modified biotinylated ddNTPs, the linkers are attached to the 5-position on the pyrimidine bases (C and T), and to the 7-position on the purines (A and G) for subsequent conjugation with biotin. It has been established that modification of these positions on the bases in the nucleotides, even with bulky energy transfer fluorescent dyes, still allows efficient incorporation of the modified nucleotides into the DNA strand by DNA polymerase (32, 33). Thus, the ddNTPs-Linker-11-biotin can be incorporated into the growing strand by the polymerase in DNA sequencing reactions.

Larger mass separations will greatly aid in longer read lengths where signal intensity is smaller and resolution is lower. The smallest mass difference between two individual bases is over three times as great in the mass tagged biotinylated ddNTPs compared to normal ddNTPs and more than double that achieved by the standard biotinylated ddNTPs as shown in Table 2.

TABLE 2

Relative mass differences (daltons) of dideoxynucleotides using ddCTP as a reference.

| Base | Standard ddNTP | Commercial Biotinylated ddNTP | Biotinylated ddNTP with mass tag linker |
| --- | --- | --- | --- |
| C relative to C | 0 | 0 | 0 (no linker) |
| T relative to C | 15 | 89 (16 linker) | 125 (Linker I) |
| A relative to C | 24 | 24 | 165 (Linker II) |
| G relative to C | 40 | 40 | 200 (Linker III) |
| Smallest relative difference | 9 | 16 | 35 |

Figure 4:
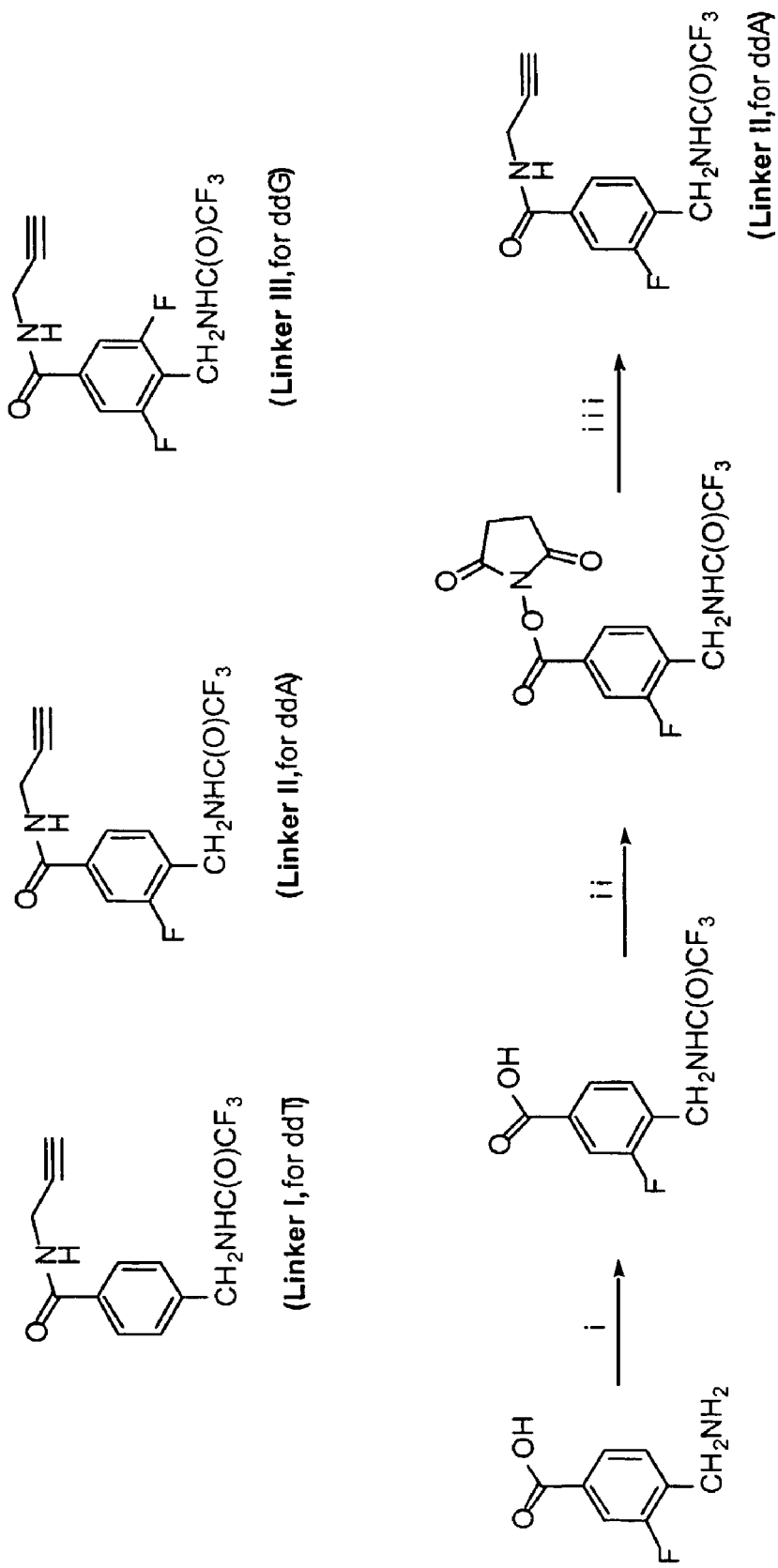
FIG. 4: Synthesis scheme for mass tag linkers. For illustrative purposes, the linkers are labeled to correspond to the specific ddNTP with which they are shown coupled in FIGS. 3, 5, 7, 8 and 9. However, any of the three linkers can be used with any ddNTP. (i) $(CF_3CO)_2O$; (ii) Disuccinimidylcarbonate/diisopropylethylamine; (iii) Propargyl amine.

Three 4-aminomethyl benzoic acid derivatives Linker I, Linker II and Linker III are designed as mass tags as well as linkers for bridging biotin to the corresponding dideoxynucleotides. The synthesis of Linker II (FIG. 4) is described here to illustrate the synthetic procedure. 3-Fluoro-4-aminomethyl benzoic acid that can be easily prepared via published procedures (41, 42) is first protected with trifluoroacetic anhydride, then converted to N-hydroxysuccinimide (NHS) ester with disuccinimidylcarbonate in the presence of diisopropylethylamine. The resulting NHS ester is subsequently coupled with commercially available propargylamine to form the desired compound, Linker II. Using an analogous procedure, Linker I and Linker III can be easily constructed.

Figure 5:
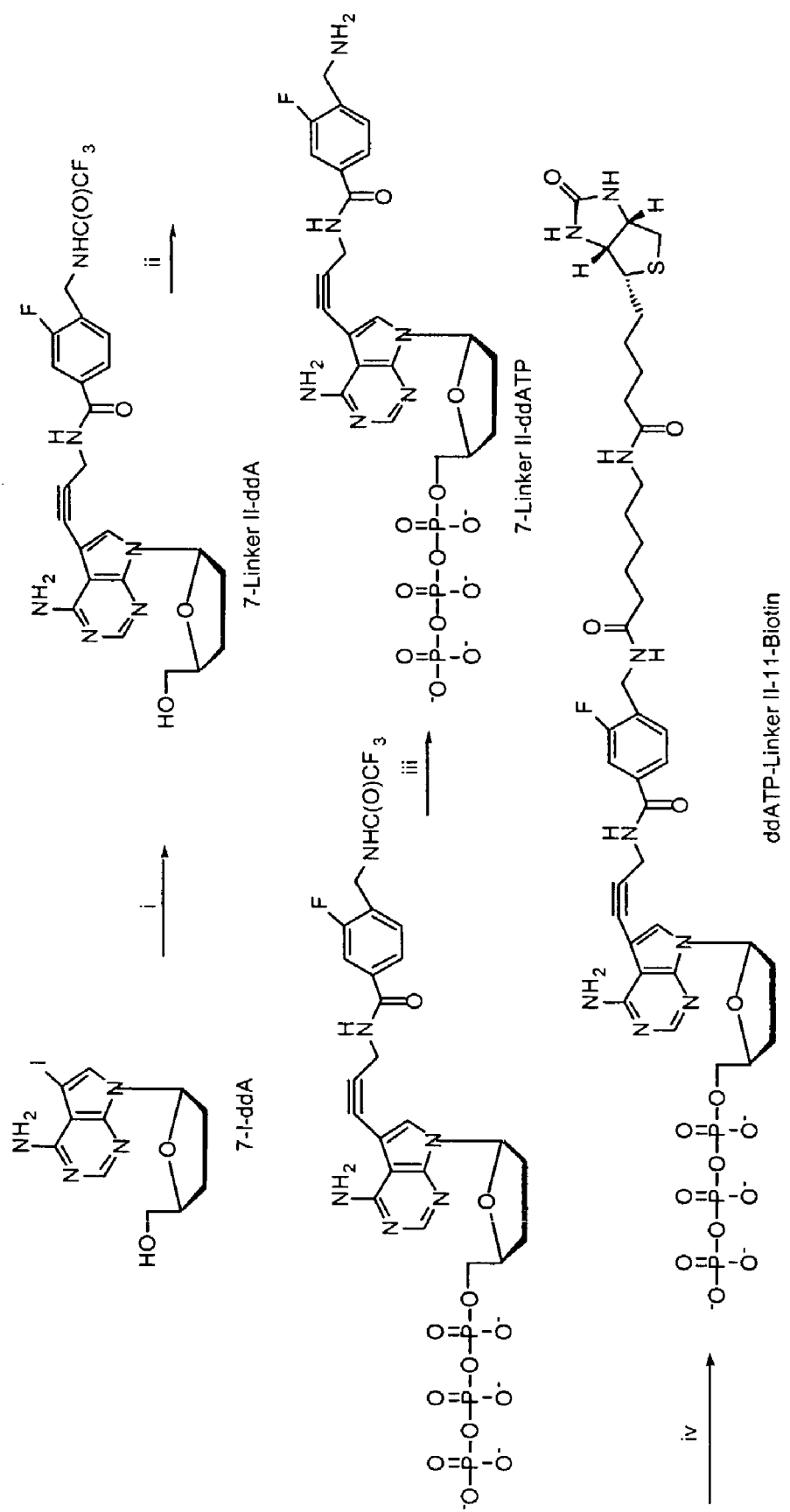
FIG. 5: The synthesis of ddATP-Linker-II-11-Biotin. (i) Linker II, tetrakis(triphenylphosphine) palladium(0); (ii) $POCl_3$, $Bn_4N^+$ pyrophosphate; (iii) $NH_4OH$; (iv) Sulfo-NHS-LC-Biotin.

FIG. 5 describes the scheme required to prepare biotinylated ddATP-Linker II-11-Biotin using well-established procedures (34–36). 7-I-ddA is coupled with linker II in the presence of tetrakis(triphenylphosphine) palladium(0) to produce 7-Linker II-ddA, which is phosphorylated with $POCl_3$ in butylammonium pyrophosphate (37). After removing the trifluoroacetyl group with ammonium hydroxide, 7-Linker II-ddATP is produced, which then couples with sulfo-NHS-LC-Biotin (Pierce, Rockford Ill.) to yield the desired ddATP-Linker II-11-Biotin. Similarly, ddTTP-Linker I-11-Biotin, and ddGTP-Linker III-11-Biotin can be synthesized.

IV. Design and Synthesis of Mass Tagged ddNTPs Containing Photocleavable Biotin

Figure 6:
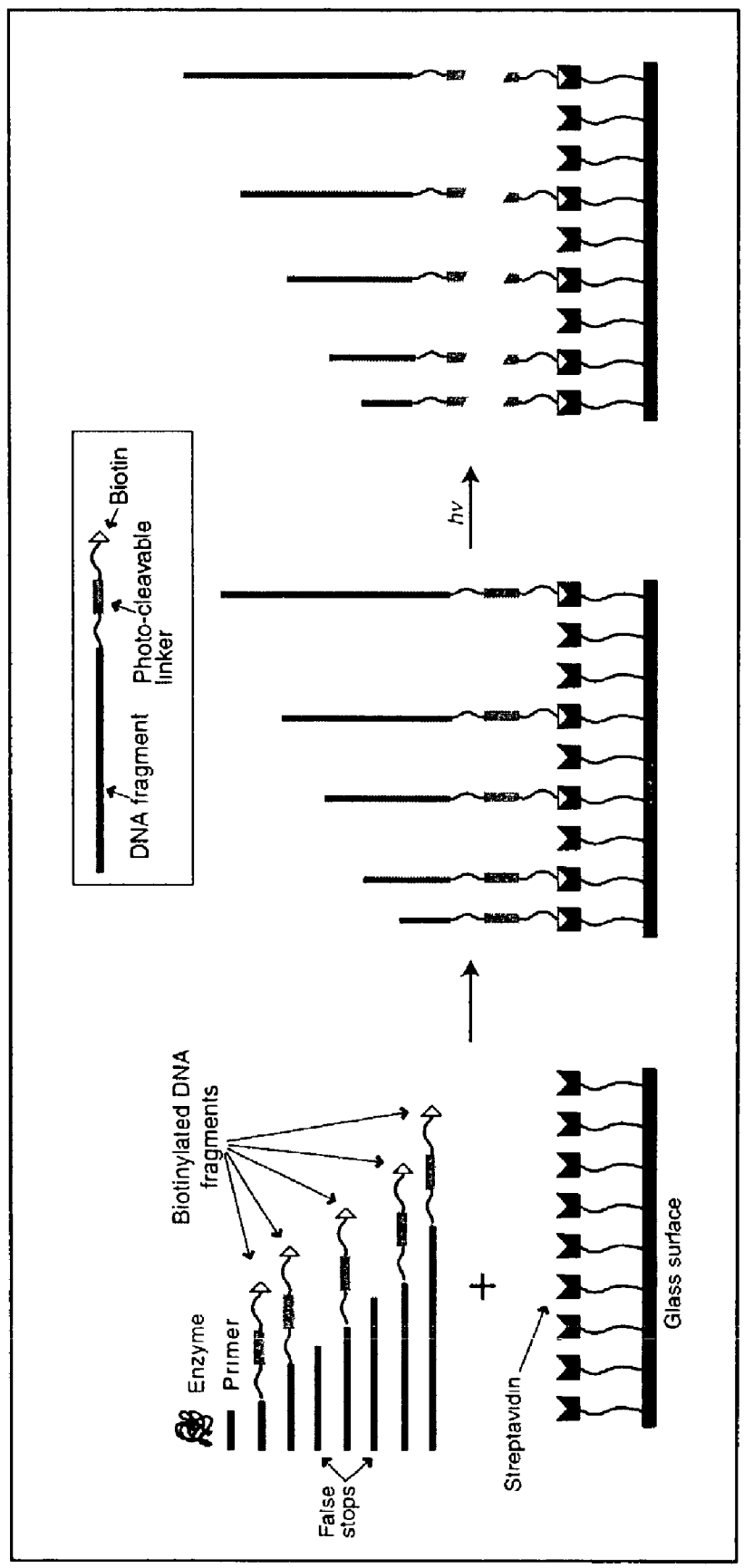
FIG. 6: DNA products are purified by a streptavidin coated porous silica surface. Only the biotinylated fragments are captured. These fragments are then cleaved by light irradiation (hv) to release the captured fragments, leaving the biotin moiety still bound to the streptavidin.
Figure 7:
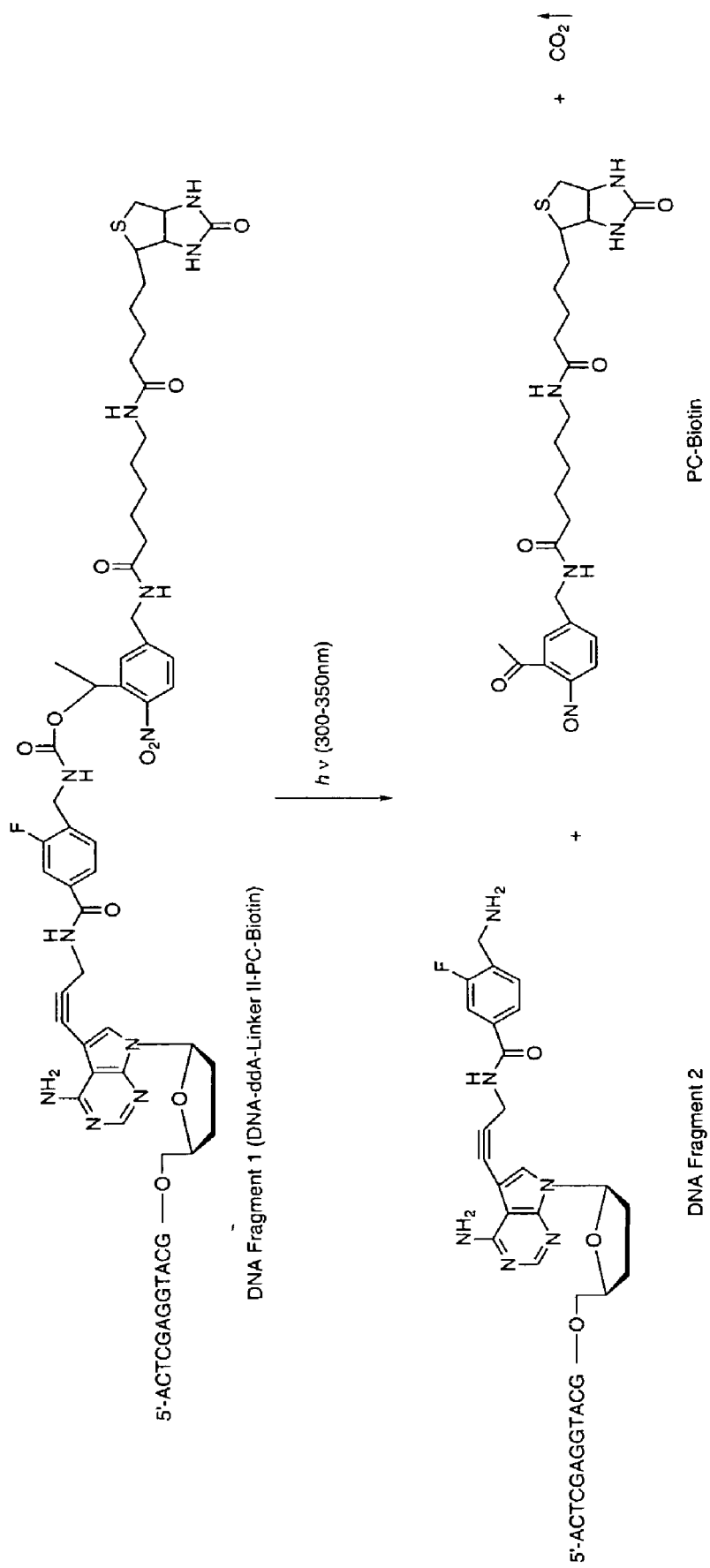
FIG. 7: Mechanism for the cleavage of photocleavable linkers.

A schematic of capture and cleavage of the photocleavable linker on the streptavidin coated porous surface is shown in FIG. 6. At the end of the reaction, the reaction mixture consists of excess primers, enzymes, salts, false stops, and the desired DNA fragment. This reaction mixture is passed over a streptavidin-coated surface and allowed to incubate. The biotinylated fragments are captured by the streptavidin surface, while everything else in the mixture is washed away. Then the fragments are released into solution by cleaving the photocleavable linker with near ultraviolet (UV) light, while the biotin remains attached to the streptavidin that is covalently bound to the surface. The pure DNA fragments can then be crystallized in matrix solution and analyzed by mass spectrometry. It is advantageous to cleave the biotin moiety since it contains sulfur which has several relatively abundant isotopes. The rest of the DNA fragments and linkers contain only carbon, nitrogen, hydrogen, oxygen, fluorine and phosphorous, whose dominant isotopes are found with a relative abundance of 99% to 100%. This allows high resolution mass spectra to be obtained. The photocleavage mechanism (38; 39) is shown in FIG. 7. Upon irradiation with ultraviolet light at 300–350 nm, the light sensitive o-nitroaromatic carbonamide functionality on DNA fragment 1 is cleaved, producing DNA fragment 2, PC-biotin and carbon dioxide. The partial chemical linker remaining on DNA fragment 2 is stable for detection by mass spectrometry.

Figure 8:
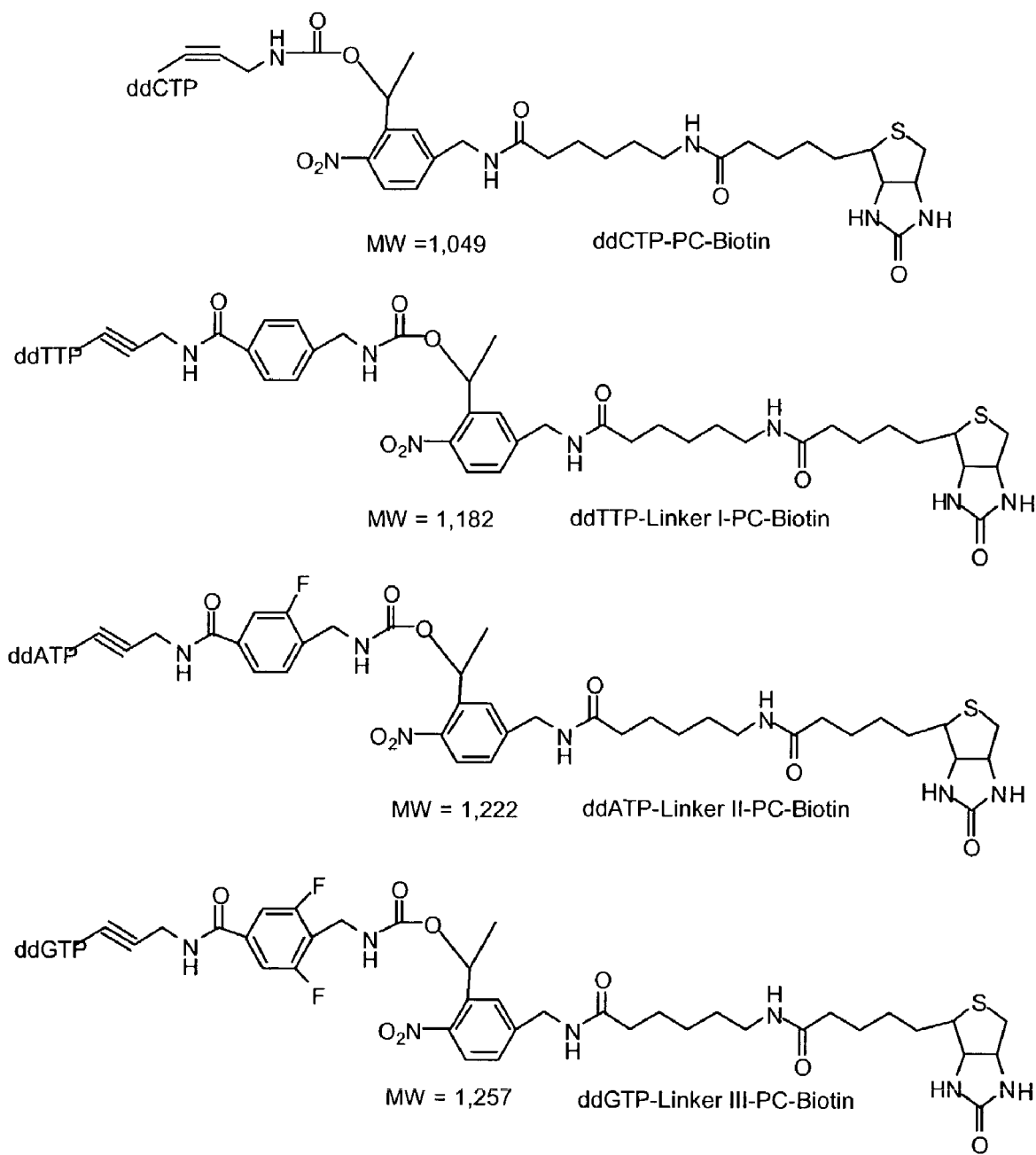
FIG. 8: The structures of ddNTPs linked to photocleavable (PC) biotin. Any of the four ddNTPs (ddATP, ddCTP, ddGTP, ddTTP) can be used with any of the shown linkers.
Figure 9:
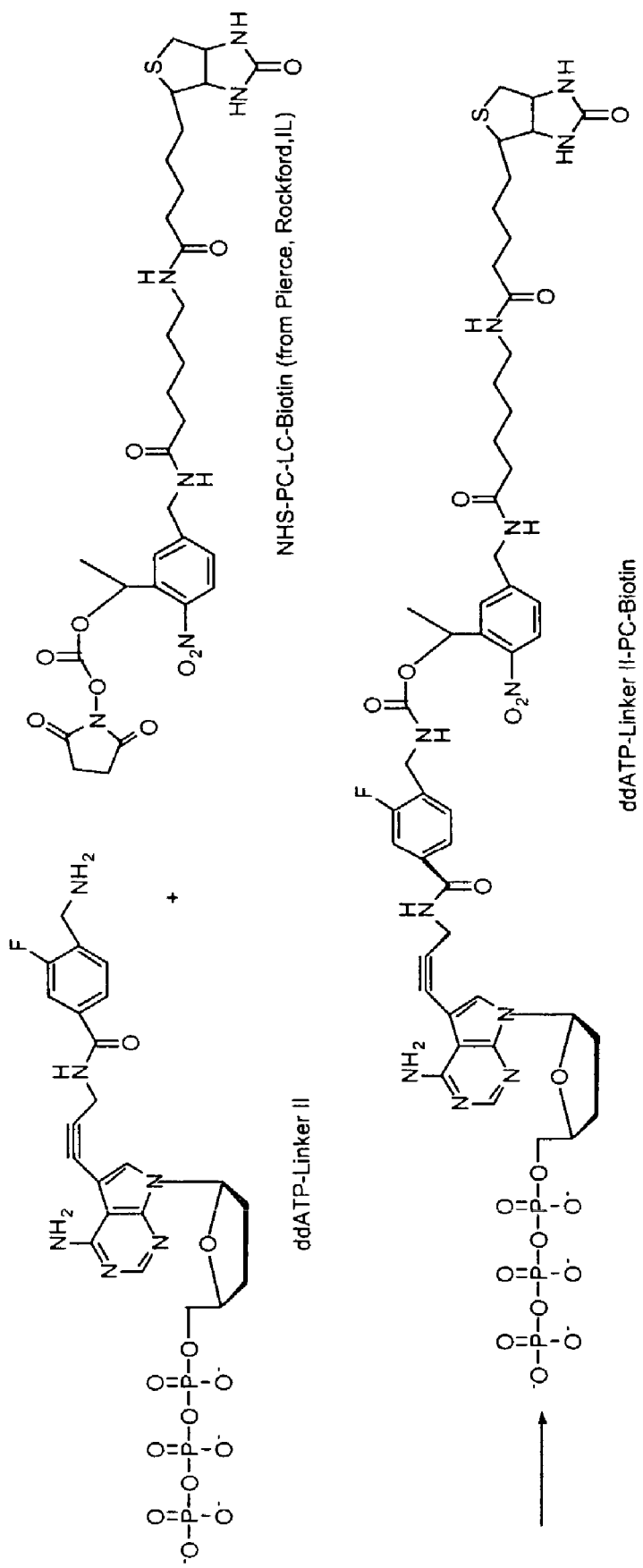
FIG. 9: The synthesis of ddATP-Linker-II-PC-Biotin. PC=photocleavable.

Four new biotinylated ddNTPs disclosed here, ddCTP-PC-Biotin, ddTTP-Linker I-PC-Biotin, ddATP-Linker II-PC-Biotin and ddGTP-Linker III-PC-Biotin are shown in FIG. 8. These compounds are synthesized by a similar chemistry as shown for the synthesis of ddATP-Linker II-11-Biotin in FIG. 6. The only difference is that in the final coupling step NHS-PC-LC-Biotin (Pierce, Rockford Ill.) is used, as shown in FIG. 9. The photocleavable linkers disclosed here allow the use of solid phase capturable terminators and mass spectrometry to be turned into a high throughput technique for DNA analysis.

Figure 10:
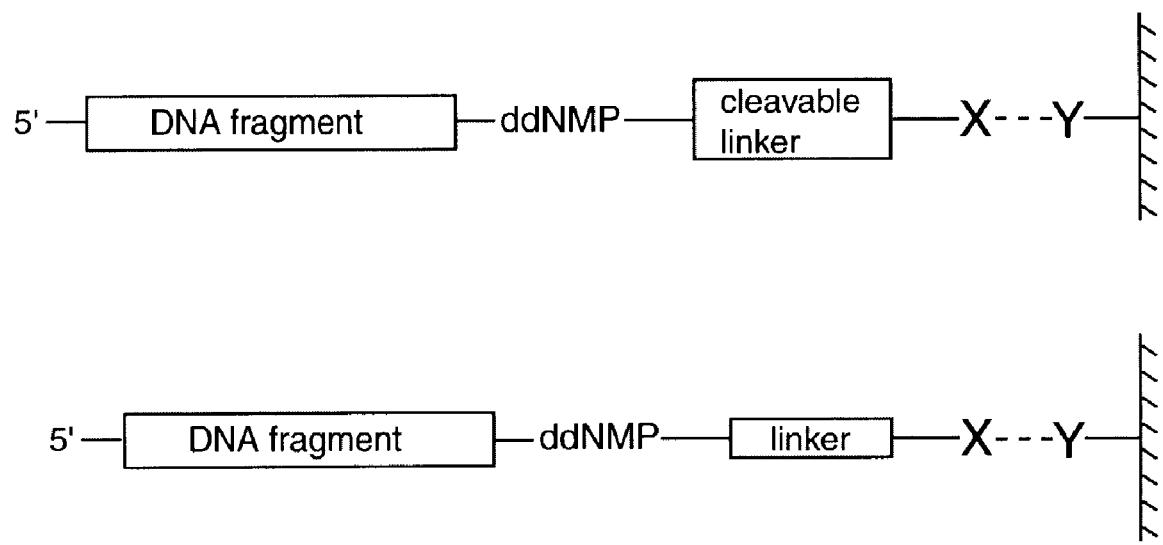
FIG. 10: Schematic for capturing a DNA fragment terminated with a dideoxynucleoside monophosphate on a surface. The dideoxynucleoside monophosphate (ddNMP) which is on the 3' end of the DNA fragment is attached via a linker to a chemical moiety "X" which interacts with a compound "Y" on the surface to capture the DNA fragment terminated with the ddNMP. The DNA fragment can be freed from the surface either by disrupting the interaction between chemical moiety X and compound Y (lower scheme) or by cleaving the linker (upper scheme).

V. Overview of Capturing a DNA Fragment Terminated with a ddNTP on a Surface and Freeing the ddNTP and DNA Fragment The DNA fragment is terminated with a dideoxynucleoside monophosphate (ddNMP). The ddNMP is attached via a linker to a chemical moiety ("X" in FIG. 10). The DNA fragment terminated with ddNMP is captured on the surface through interaction between chemical moiety "X" and a compound on or attached to the surface ("Y" in FIG. 10). The present application discloses two methods for freeing the captured DNA fragment terminated with ddNMP. In the situation illustrated in the lower part of FIG. 10, the DNA fragment terminated with ddNMP is freed from the surface by disrupting or breaking the interaction between chemical moiety "X" and compound "% Y". In the upper part of FIG. 10, the DNA fragment terminated with ddNMP is attached to chemical moiety "X" via a cleavable linker which can be cleaved to free the DNA fragment terminated with ddNMP.

Different moieties and compounds can be used for the "X"-"Y" affinity system, which include but are not limited to, biotin-streptavidin, phenylboronic acid-salicylhydroxamic acid (31), and antigen-antibody systems.

In different embodiments, the cleavable linker can be cleaved and the "X"-"Y" interaction can be disrupted by a means selected from the group consisting of one or more of a physical means, a chemical means, a physical chemical means, heat, and light. In one embodiment, ultraviolet light can be used to cleave the cleavable linker. Chemical means include, but are not limited to, ammonium hydroxide (40), formamide, or a change in pH (−log H$^+$ concentration) of the solution.

VI. High Density Streptavidin-coated, Porous Silica Channel System.

Streptavidin coated magnetic beads are not ideal for using the photocleavable biotin capture and release process for DNA fragments, since they are not transparent to UV light. Therefore, the photocleavage reaction is not efficient. For efficient capture of the biotinylated fragments, a high-density surface coated with streptavidin is essential. It is known that the commercially available 96-well streptavidin coated plates cannot provide a sufficient surface area for efficient capture of the biotinylated DNA fragments. Disclosed in this application is a porous silica channel system designed to overcome this limitation.

Figure 11:
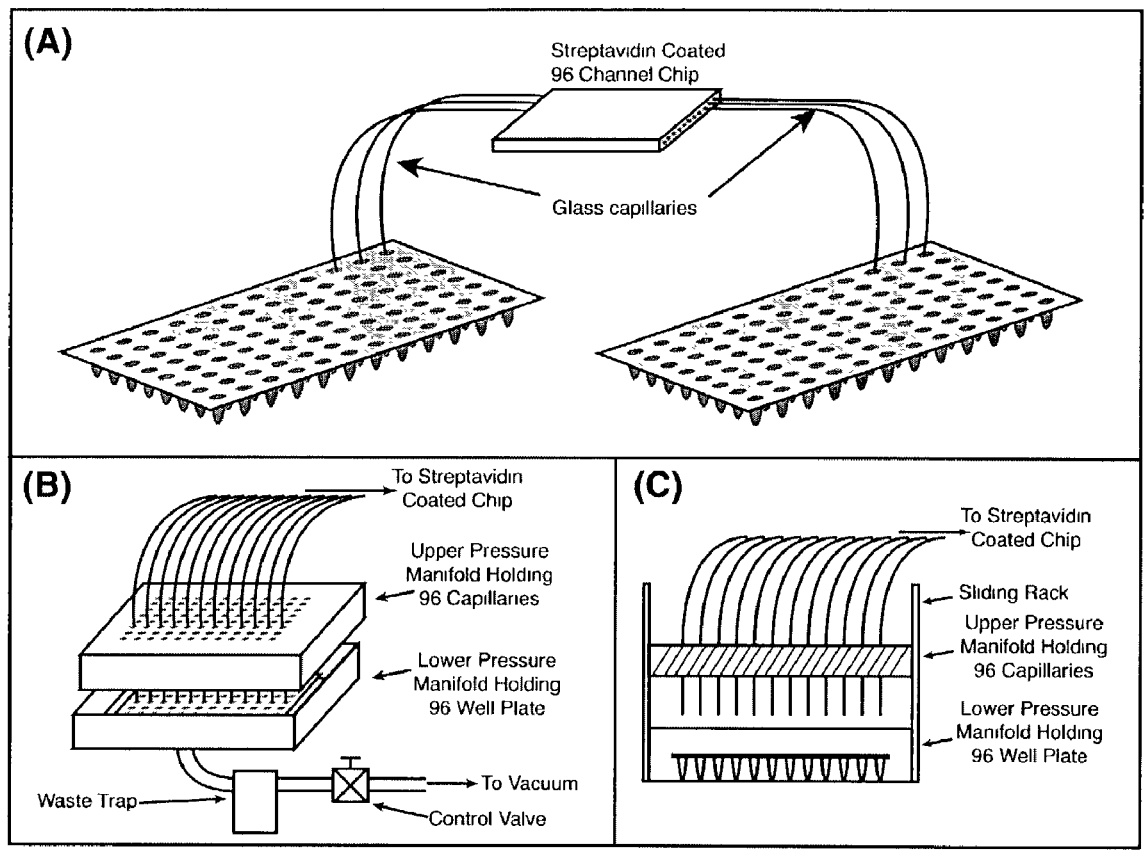
FIGS. 11A–11C: Schematic of a high throughput channel based purification system. Sample solutions can be pushed back and forth between the two plates through glass capillaries and the streptavidin coated channels in the chip. The whole chip can be irradiated to cleave the samples after immobilization.
Figure 12:
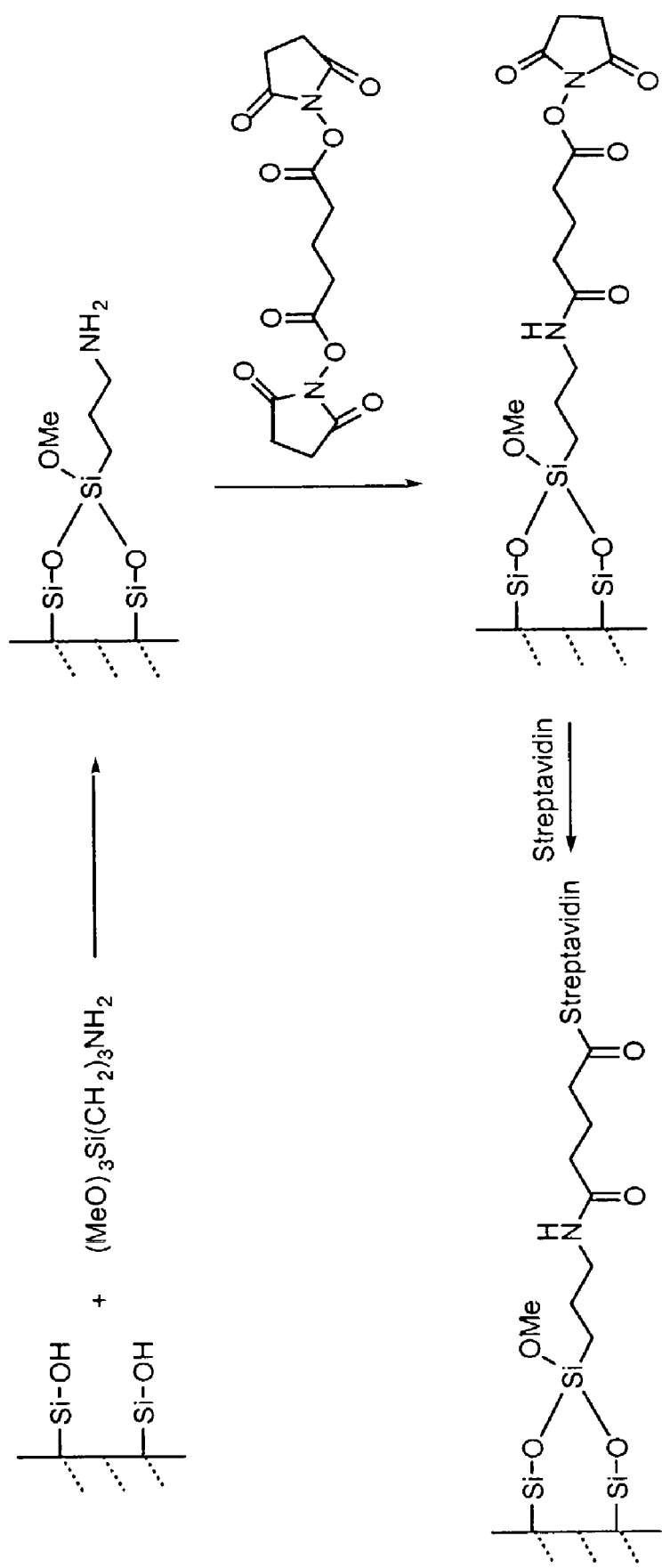
FIG. 12: The synthesis of streptavidin coated porous surface.

To increase the surface area available for solid phase capture, porous channels are coated with a high density of streptavidin. For example, ninety-six (96) porous silica glass channels can be etched into a silica chip (FIG. 11). The surfaces of the channels are modified to contain streptavidin as shown in FIG. 12. The channel is first treated with 0.5 M NaOH, washed with water, and then briefly pre-etched with dilute hydrogen fluoride. Upon cleaning with water, the capillary channel is coated with high density 3-aminopropyltrimethoxysilane in aqueous ethanol (43). An excess of disuccinimidyl glutarate in N,N-dimethylformamide (DMF) is then introduced into the capillary to ensure a highly efficient conversion of the surface end group to a succinimidyl ester. Streptavidin is then conjugated with the succinimidyl ester to form a high-density surface using excess streptavidin solution. The resulting 96-channel chip is used as a purification cassette.

A 96-well plate that can be used with biotinylated terminators for DNA analysis is shown in FIG. 11. In the example shown, each end of a channel is connected to a single well. However, for other applications, the end of a channel could be connected to a plurality of wells. Pressure is applied to drive the samples through a glass capillary into the channels on the chip. Inside the channels the biotin is captured by the covalently bound streptavidin. After passing through the channel, the sample enters into a clean plate in the other end of the chip. Pressure applied in reverse drives the sample through the channel multiple times and ensures a highly efficient solid phase capture. Water is similarly added to drive out the reaction mixture and thoroughly wash the captured fragments. After washing, the chip is irradiated with ultraviolet light to cleave the photosensitive linker and release the DNA fragments. The fragment solution is then driven out of the channel and into a collection plate. After matrix solution is added, the samples are spotted on a chip and allowed to crystallize for detection by MALDI-TOF mass spectrometry. The purification cassette is cleaned by chemically cleaving the biotin-streptavidin linkage, and is then washed and reused.

REFERENCES

1) Kwok, P. -Y. (2000) Pharmacogenomics 1, 95–100.
2) Roses A. (2000) Pharmacogenetics and the practice of medicine. *Nature*. 405: 857–865.
3) The International SNP Map Working Group (2001) Nature 409, 928–933.
4) Beavis, R. C. & Chait, B. T. (1989) Rapid Commun. Mass Spectrom. 3, 436–439.
5) Li, J., Butler, J. M., Tan, Y., Lin, H., Royer, S., Ohler, L., Shaler, T. A., Hunter, J. A., Pollart, D. J., Monforte, J. A. & Becker, C. H. (1999) Electrophoresis 20, 1258–1265.
6) Griffin, T. J. & Smith, L. M. (2000) Trends. Biotechnol. 18, 77–84.
7) Graber, J. H., Smith, C. L. & Cantor, C. R. (1999) Genetic Analysis: Biomol. Eng. 14, 215–219.
8) Stoerker, J., Mayo, J. D., Tetzlaff, C. N., Sarracino, D. A., Schwope, I. & Richert, C. (2000) Nat. Biotechnol. 18, 1213–1216.
9) Ross, P. L., Lee, K. & Belgrader, P. (1997) Anal. Chem. 69, 4197–4202.
10) Jiang-Baucom, P., Girard, J. E., Butler, J. & Belgrader, P. (1997) Anal. Chem. 69, 4894–4898.
11) Griffin, T. J., Hall, J. G., Prudent, J. R. & Smith, L. M. (1999) Proc. Natl. Acad. Sci. USA. 96, 6301–6306.
12) Lyamichev, V., Mast, A. L., Hall, J. G., Prudent, J. R., Kaiser, M. W., Takova, T., Kwiatkowski, R. W., Sander, T. J., de Arruda, M., Arco, D. A., Neri, B. P. & Brow, M. A. D. (1999) Nat. Biotechnol. 17, 292–296.
13) Haff, L. A. & Smirnov, I. P. (1997) Nucleic Acids Res. 25, 3749–3750.
14) Ross, P., Hall, L., Smirnov, I. P. & Haff, L. (1998) Nat. Biotechnol. 16, 1347–1351.
15) Fei Z, Ono T, Smith LM. (1998) MALDI-TOF mass spectrometric typing of single nucleotide polymorphisms with mass-tagged ddNTPs. *Nucleic Acids Res.* 26: 2827–2828.
16) Tang K, Fu D J, Julien D, Braun A, Cantor C R, Koster H. (1999) Chip-based genotyping by mass spectrometry. *Proc. Natl. Acad. Sci. USA*. 96: 10016–10020.
17) Taranenko, N. I., Allman, S. L., Golovlev, V. V., Taranenko, N. V., Isola, N. R. & Chen, C. H. (1998) Nucleic Acids Res. 26, 2488–2490.
18) Ju J. Nucleic Acid Sequencing with Solid Phase Capturable Terminators. U.S. Pat. No. 5,876,936, issued Mar. 2, 1999.
19) Edwards, J. R., Itagaki, Y. & Ju, J. (2001) Nucleic Acids Res. 29, e104 (p1–5).
20) Tong, A. K. & Ju, J. (2002) Single nucleotide polymorphism detection by combinatorial fluorescence energy transfer tags and biotinylated dideoxynucleotides. Nucleic Acids Res. 30(5):e19.
21) Roskey M T, Juhasz P, Smirnov I P, Takach E J, Martin S A, Haff L A. (1996) DNA sequencing by delayed extraction-matrix-assisted laser desorption/ionization time of flight mass spectrometry. *Proc. Natl. Acad. Sci. USA*. 93: 4724–4729.
22) Hanson, E. H., Imperatore, G. & Burke, W. (2001) Am. J. Epidem. 154, 193–206.
23) Langer P R, Waldrop A A, Ward D C. (1981) Enzymatic synthesis of biotin-labeled polynucleotides: novel nucleic acid affinity probes. *Proc. Natl. Acad. Sci. USA*. 78: 6633–6637.
24) Hawkins, T. L., O'Connor-Morin, T., Roy, A. & Santillan, C. (1994) Nucleic Acids Res. 22, 4543–4544.
25) Uhlen, M. (1989) Nature, 340, 733–734.
26) Wahlberg, J., Lunderberg, J., Hultman, T. & Uhlen, M. (1990) Proc. Natl. Acad. Sci. USA. 87, 6569–6573.
27) Tong, X., Smith L M (1992) Solid-Phase Method for the Purification of DNA Sequencing Reactions. *Anal. Chem.* 64: 2672–2677.

28) Schneider K, Chait B T. (1995) Increased stability of nucleic acids containing 7-deaza-guanosine and 7-deaza-adenosine may enable rapid DNA sequencing by matrix-assisted laser desorption mass spectrometry. *Nucleic Acids Res.* 23: 1570–1575.
29) Monforte J A, Becker C H (1997) High-throughput DNA analysis by time-of-flight mass spectrometry. *Nat Medicine.* 3(3): 360–362.
30) Hilton, G. C., Martinis, J. M., Wollman, D. A., Irwin, K. D., Dulcie, L. L., Gerber, D., Gillevet, P. M. & Twerenbold, D. (1998) Nature 391, 672–675.
31) Bergseid M, Baytan A R, Wiley J P, Ankener W M, Stolowitz, Hughs K A, Chestnut J D (November 2000) Small-molecule base chemical affinity system for the purification of proteins. *BioTechniques* 29: 1126–1133.
32) Rosenblum B B, Lee L G, Spurgeon S L, Khan S H, Menchen S M, Heiner C R, Chen S M. (1997) New dye-labeled terminators for improved DNA sequencing patterns. *Nucleic Acids Res.* 25: 4500–4504.
33) Zhu Z, Chao J, Yu H, Waggoner A S. (1994) Directly labeled DNA probes using fluorescent nucleotides with different length linkers. *Nucleic Acids Res.* 22: 3418–3422.
34) Prober J M, Trainor G L, Dam R J, Hobbs F W, Robertson C W, Zagursky R J, Cocuzza A J, Jensen M A, Baumeister K. (1987) A system for rapid DNA sequencing with fluorescent chain-terminating dideoxynucleotides. *Science* 238: 336–341.
35) Lee L G, Connell C R, Woo S L, Cheng R D, Mcardle B F, Fuller C W, Halloran N D, Wilson R K. (1992) DNA sequencing with dye-labeled terminators and T7 DNA-polymerase-effect of dyes and dNTPs on incorporation of dye-terminators and probability analysis of termination fragments. *Nucleic Acids Res.* 20: 2471–2483.
36) Hobbs F W Jr, Cocuzza A J. Alkynylamino-Nucleotides. U.S. Pat. No. 5,047,519, issued Sep. 10, 1991.
37) Burgess K, Cook D. (2000) *Chemical Reviews.* 100: 2047–2060.
38) Olejnik J, Sonar S, Krzymanska-Olejnik E, Rothschild K J. (1995) Photocleavable biotin derivatives: a versatile approach for the isolation of biomolecules. *Proc. Natl. Acad. Sci. USA.* 92: 7590–7594.
39) Olejnik J, Ludemann H C, Krzymanska-Olejnik E, Berkenkamp S, Hillenkamp F, Rothschild K J. (1999) Photocleavable peptide-DNA conjugates: synthesis and applications to DNA analysis using MALDI-MS. *Nucleic Acids Res.* 27: 4626–4631.
40) Jurinke C, van de Boom D, Collazo V, Luchow A, Jacob A, Koster H. (1997) Recovery of nucleic acids from immobilized biotin-streptavidin complexes using ammonium hydroxide and applications in MALDI-TOF mass spectrometry. *Anal. Chem.* 69: 904–910.
41) Maudling D R, Lotts K D, Robinson S A. (1983) New procedure for making 2-(chloromethyl)-4-nitrotoluene. *J. Org. Chem.* 48: 2938.
42) Rolla F. (1982) Sodium-borohydride reactions under phase-transfer conditions—reduction of azides to amines. *J. Org. Chem.* 47: 4327–4329.
43) Woolley A T, Mathies R A. (1994) Ultra-high-speed DNA fragment separations using microfabricated capillary array electrophoresis chips. *Proc. Natl. Acad. Sci. USA.* 91: 11348–11352.

What is claimed is:

1. A method for determining the identity of a nucleotide present at a predetermined site in a DNA whose sequence immediately 3' of such predetermined site is known which comprises:

(a) treating the DNA with an oligonucleotide primer whose sequence is complementary to such known sequence so that the oligonucleotide primer hybridizes to the DNA and forms a complex in which the 3' end of the oligonucleotide primer is located immediately adjacent to the predetermined site in the DNA;

(b) simultaneously contacting the complex from step (a) with four different dideoxynucleotides each photocleavably attached to a label, in the presence of a polymerase under conditions permitting a labeled dideoxynucleotide to be added to the 3' end of the primer so as to generate a labeled single base extended primer, wherein each of the four different labeled dideoxynucleotides (i) is complementary to one of the four nucleotides present in the DNA and (ii) has a molecular weight which can be distinguished from the molecular weight of the other three labeled dideoxynucleotides using mass spectrometry;

(c) (i) contacting the labeled single base extended primer with a solid surface coated with a compound that specifically interacts with the label attached to the dideoxynucleotide so as to thereby capture the extended primer on the surface, (ii) removing primers that have not been extended by a labeled dideoxynucleotide, and (iii) photocleaving the captured labeled single base extended primer so as to release it from the surface; and (d) determining the difference in molecular weight between the labeled single base extended primer and the oligonucleotide primer so as to identify the dideoxynucleotide incorporated into the single base extended primer and thereby determine the identity of the nucleotide present at the predetermined site in the DNA.

2. The method of claim 1, wherein each of the four labeled dideoxynucleotides comprises a chemical moiety attached to the dideoxynucleotide by a different linker which has a molecular weight different from that of each other linker.

3. The method of claim 1, wherein step (d) comprises determining the difference in mass between the labeled single base extended primer and an internal mass calibration standard added to the extended primer.

4. The method of claim 1, wherein the interaction between the label attached to the dideoxynucleotide by the linker and the compound on the surface comprises a biotin-streptavidin interaction, a phenylboronic acid-salicylhydroxamic acid interaction, or an antigen-antibody interaction.

5. The method of claim 1, wherein the linker is attached to the dideoxynucleotide at the 5-position of cytosine or thymine or at the 7-position of adenine or guanine.

6. The method of claim 1, wherein the linker comprises a derivative of 4-aminomethyl benzoic acid, a 2-nitrobenzyl group, or a derivative of a 2-nitrobenzyl group.

7. The method of claim 6, wherein the linker comprises one or more fluorine atoms.

8. The method of claim 7, wherein the linker is selected from the group consisting of:

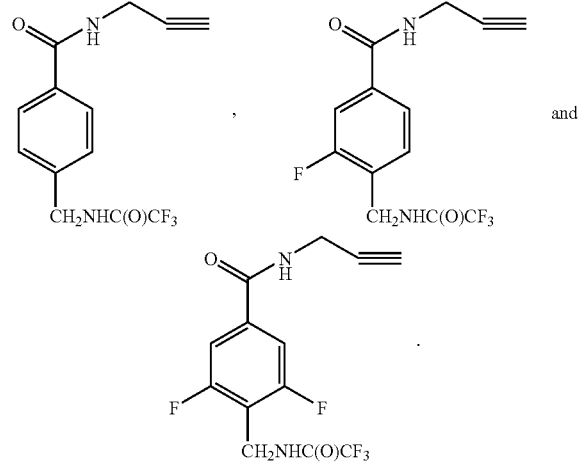

9. The method of claim 1, wherein the label comprises biotin, the labeled dideoxynucleotide is a biotinylated dideoxynucleotide, the labeled single base extended primer is a biotinylated single base extended primer, and the surface is a streptavidin-coated solid surface.

10. The method of claim 9, wherein the biotinylated dideoxynucleotide is selected from the group consisting of ddATP-11-biotin, ddCTP-11-biotin, ddGTP-11-biotin, and ddTTP-16-biotin.

11. The method of claim 9, wherein the biotinylated dideoxynucleotide is selected from the group consisting of:

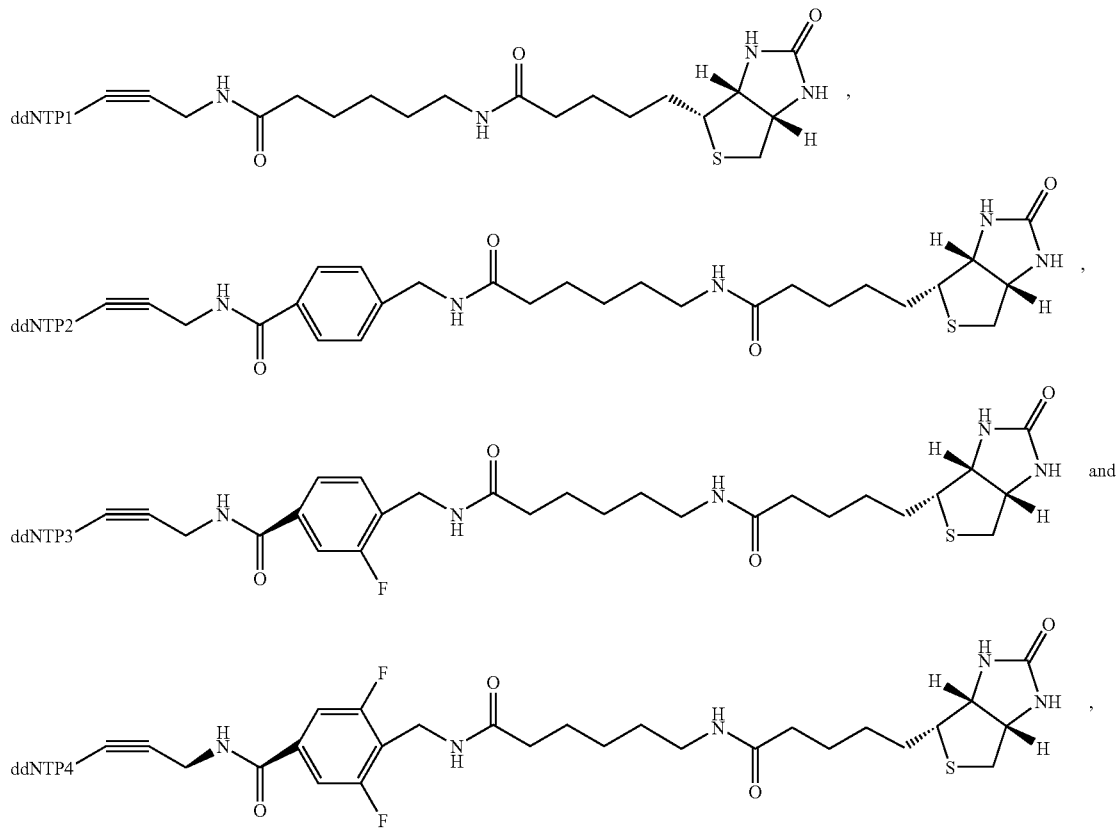

wherein ddNTP1, ddNTP2, ddNTP3, and ddNTP4 represent four different dideoxynucleotides.
12. The method of claim 11, wherein the biotinylated dideoxynucleotide is selected from the group consisting of:
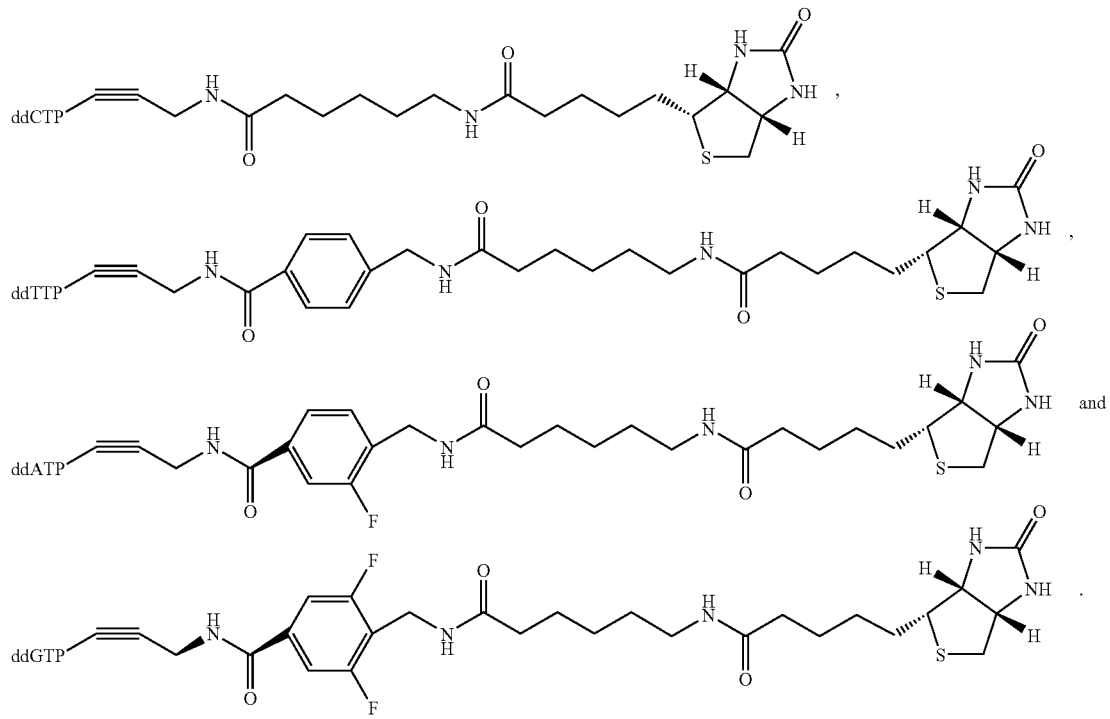
13. The method of claim 9, wherein the biotinylated dideoxynucleotide is selected from the group consisting of:
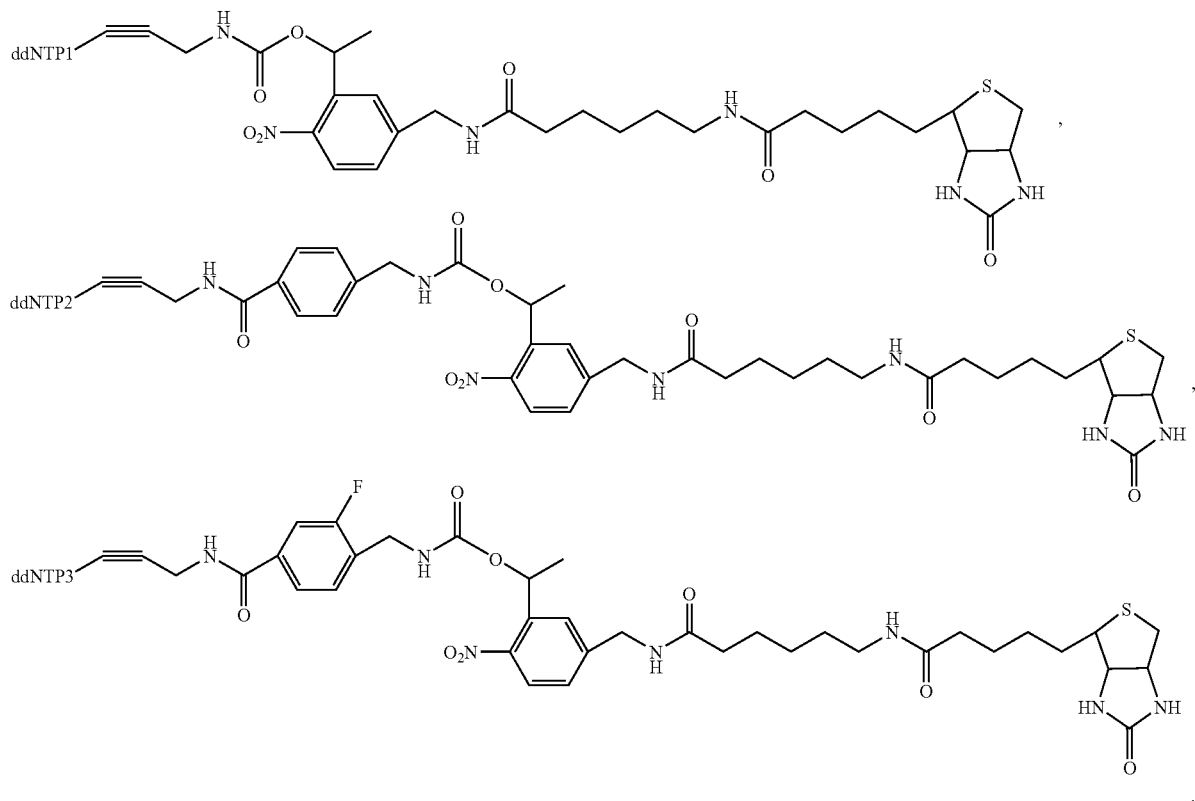

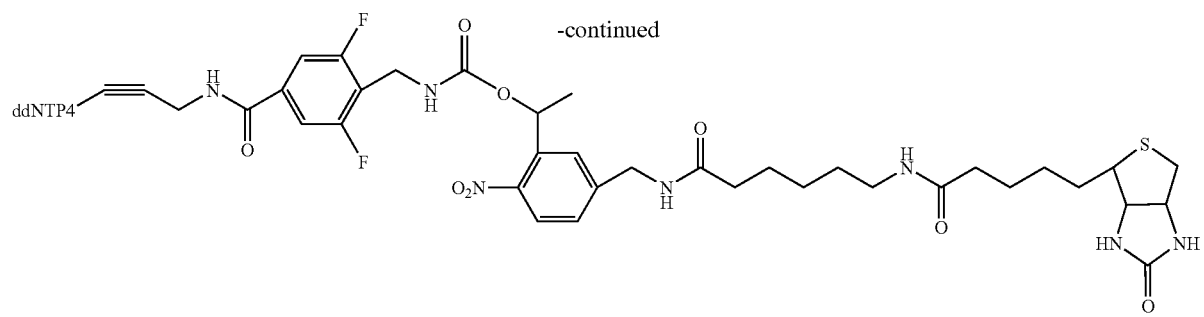
wherein ddNTP1, ddNTP2, ddNTP3, and ddNTP4 represent four different dideoxynucleotides.
14. The method of claim 13, wherein the biotinylated dideoxynucleotide is selected from the group consisting of:
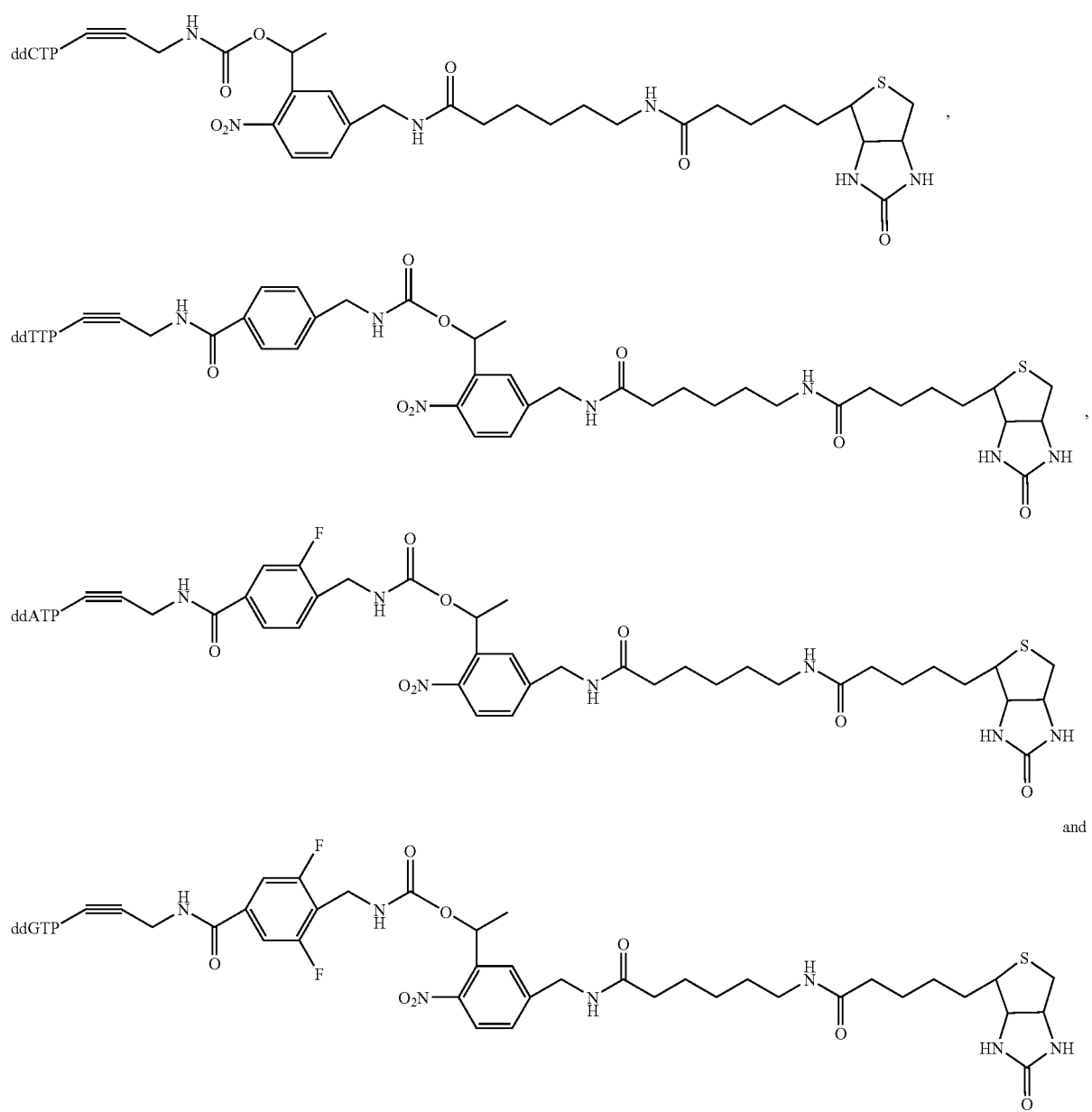

15. The method of claim 9, wherein the streptavidin-coated solid surface is a streptavidin-coated magnetic bead or a streptavidin-coated silica glass.

16. The method of claim 1, wherein steps (a) and (b) are performed in a single container or in a plurality of connected containers.

17. A method for determining the identity of nucleotides present at a plurality of predetermined sites, which comprises carrying out the method of claim 1 using a plurality of different primers each having a molecular weight different from that of each other primer, wherein each primer hybridizes adjacent to a different predetermined site.

18. The method of claim 17, wherein different linkers each having a molecular weight different from that of each other linker are attached to the different dideoxynucleotides to increase mass separation between different labeled single base extended primers and thereby increase mass spectrometry resolution.

* * * * *

```
                             SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1 ctaccccag aacatcacc                                                     19

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
gcactacctc ttcatgggtg cc                                                22

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
catcagtcac atacccca                                                     18
```

```
<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cagtgaacat gtgatcccac cc                                              22

<210> SEQ ID NO 5
<211> LENGTH: 13
<212> TYPE: DNA
<213> ORGANISM: Artificial Sequence
<220> FEATURE:
<223> OTHER INFORMATION: internal mass standard

<400> SEQUENCE: 5
tttttctttt tct                                                        13

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ggggaagagc agagatatac gt                                              22

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ggggctccac acggcgactc tcat                                            24

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
agaggatcca accgagac                                                   18

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
tggtggtagg tgatgttgat gta                                             23

<210> SEQ ID NO 10
<211> LENGTH: 22
<212> TYPE: DNA
<213> ORGANISM: Artificial Sequence
<220> FEATURE:
```

```
-continued

<223> OTHER INFORMATION: primer

<400> SEQUENCE: 10
cacattgtca aggacgtacc cg                                              22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tacccgccgt acttggcctc                                                 20

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
tccacgcaca aacacggaca g                                               21

<210> SEQ ID NO 13
<211> LENGTH: 100
<212> TYPE: DNA
<213> ORGANISM: Artificial Sequence
<220> FEATURE:
<223> OTHER INFORMATION: template

<400> SEQUENCE: 13
taccckgagg ccaagtacgg cgggtacgtc cttgacaatg tgtacatcaa catcacctac     60
caccatgtca gtctcggttg gatcctctat tgtgtccggg                          100

<210> SEQ ID NO 14
<211> LENGTH: 110
<212> TYPE: DNA
<213> ORGANISM: Artificial Sequence
<220> FEATURE:
<223> OTHER INFORMATION: template

<400> SEQUENCE: 14
gaaggagaca cgcggccaga gagggtcctg tccgtgtttg tgcgtggagt ttcgacaagg     60
cagggtcatc taatggtgat gagtcctatc cttttctctt cgttctccgt               110
```